US008864670B2

(12) United States Patent
Lisiecki et al.

(10) Patent No.: US 8,864,670 B2
(45) Date of Patent: Oct. 21, 2014

(54) ULTRASONIC MONITORING DEVICE FOR MEASURING PHYSIOLOGICAL PARAMETERS OF A MAMMAL

(75) Inventors: Ronald S. Lisiecki, Libertyville, IL (US); Tamas Ban, Round Lake Beach, IL (US)

(73) Assignee: Hospira, Inc., Lake Forest, IL (US)

( * ) Notice: Subject to any disclaimer, the term of this patent is extended or adjusted under 35 U.S.C. 154(b) by 371 days.

(21) Appl. No.: 13/358,609

(22) Filed: Jan. 26, 2012

(65) Prior Publication Data

US 2012/0197118 A1 Aug. 2, 2012

Related U.S. Application Data

(60) Provisional application No. 61/437,047, filed on Jan. 28, 2011.

(51) Int. Cl.
*A61B 8/00* (2006.01)
*A61B 5/00* (2006.01)
*A61B 8/08* (2006.01)
*A61B 8/04* (2006.01)
*A61B 5/021* (2006.01)

(52) U.S. Cl.
CPC ............. *A61B 8/0891* (2013.01); *A61B 5/6822* (2013.01); *A61B 8/04* (2013.01); *A61B 8/4236* (2013.01); *A61B 2562/046* (2013.01); *A61B 5/6833* (2013.01); *A61B 2560/0412* (2013.01); *A61B 8/4483* (2013.01); *A61B 5/02141* (2013.01)
USPC ............................ 600/438; 600/459; 600/485

(58) Field of Classification Search
USPC .................................................. 600/438, 485
See application file for complete search history.

(56) References Cited

U.S. PATENT DOCUMENTS

| 4,072,146 A | 2/1978 | Howes |
| 4,852,578 A | 8/1989 | Campanion et al. |
| 4,986,277 A * | 1/1991 | Sackner .................... 600/485 |
| 5,058,591 A | 10/1991 | Campanion et al. |
| 5,235,985 A | 8/1993 | McMorrow et al. |

(Continued)

FOREIGN PATENT DOCUMENTS

WO 00/28899 A1 5/2000

OTHER PUBLICATIONS

Lipton, B. "Estimation of central venous pressure by ultrasound of internal jugular vein" American. Journal of Emergency Medicine. Jul. 2000; 18(4):432-4.*

(Continued)

*Primary Examiner* — Jonathan Cwern
(74) *Attorney, Agent, or Firm* — Michael R. Crabb

(57) ABSTRACT

An ultrasonic monitoring device includes a substrate, a plurality of ultrasonic transducer elements, a computer readable memory medium, a microprocessor, and a power source. The ultrasonic transducer elements are coupled to the substrate. Each ultrasonic transducer element is separately configured to transmit a signal to a target area of a mammal and to receive an echo return signal from the target area. The computer readable memory medium includes program instructions. The microprocessor is coupled to the ultrasonic transducer elements and to the computer readable memory medium for executing the program instructions to determine a physiological parameter of the mammal based on a combined analysis of the echo return signals received by the ultrasonic transducer elements. The power source is coupled to at least one of the ultrasonic transducer elements, the computer readable memory medium, or the microprocessor for supplying electrical energy.

21 Claims, 19 Drawing Sheets

(56) References Cited

U.S. PATENT DOCUMENTS

| | | | |
|---|---|---|---|
| 5,598,845 | A | 2/1997 | Chandraratna |
| 5,964,710 | A | 10/1999 | Ganguly et al. |
| 6,176,832 | B1 | 1/2001 | Habu et al. |
| 6,359,190 | B1 | 3/2002 | Ter-Ovanesyan et al. |
| 6,554,774 | B1 | 4/2003 | Miele |
| 6,579,247 | B1 | 6/2003 | Abramovitch et al. |
| 6,790,178 | B1 | 9/2004 | Mault et al. |
| 6,858,006 | B2 | 2/2005 | MacCarter et al. |
| 6,911,912 | B2 | 6/2005 | Roe et al. |
| 7,125,383 | B2 | 10/2006 | Hoctor et al. |
| 7,425,199 | B2 | 9/2008 | Hoctor et al. |
| 7,747,301 | B2 | 6/2010 | Cheng |
| 7,751,868 | B2 | 7/2010 | Glossop et al. |
| 7,857,763 | B2 | 12/2010 | Tai |
| 2001/0015591 | A1 | 8/2001 | Yoshida |
| 2005/0154320 | A1 | 7/2005 | Froelich et al. |
| 2007/0016053 | A1 | 1/2007 | Lo et al. |
| 2007/0123778 | A1 | 5/2007 | Kantorovich |
| 2007/0123779 | A1 | 5/2007 | Hoctor et al. |
| 2007/0167768 | A1 | 7/2007 | Kristiansen |
| 2007/0239041 | A1* | 10/2007 | Chatterjee et al. ............ 600/453 |
| 2007/0270720 | A1* | 11/2007 | Fry ................ 600/587 |
| 2008/0064953 | A1 | 3/2008 | Falco et al. |
| 2008/0091090 | A1 | 4/2008 | Guillory |
| 2008/0208057 | A1 | 8/2008 | Hoctor et al. |
| 2008/0294047 | A1 | 11/2008 | Kodama et al. |
| 2009/0149751 | A1 | 6/2009 | Mourad et al. |
| 2009/0326352 | A1* | 12/2009 | Cheng ........................... 600/324 |
| 2010/0234716 | A1 | 9/2010 | Engel |

OTHER PUBLICATIONS

Baumann U, Marquis C, Stoupis C, Willenberg T A, Takala J, Jakob S M. "Estimation of central venous pressure by ultrasound". Resuscitation. 64(2005), 193-199.*

MSDS for Graham-Field Ultrasound Gel, G F Health Products, Inc., Aug. 13, 2003, pp. 1-4, Atlanta, Georgia.

MSDS for Wavelength Clear Ultrasound Gel, National Therapy Products Inc., Jan. 1, 2003, pp. 1-4, Woodbridge, Ontario, Canada.

MSDS for Aquasonic Clear Ultrasound Gel, Parker Laboratories, Inc., Sep. 2009, pp. 1-2, Fairfield, New Jersey.

Inglis, G., et al., Establishing normal values of central venous pressure in very low birth weight infants. Physiological Measurement, 2007. vol. 28, No. 10.

* cited by examiner

ULTRASONIC MONITORING DEVICE FOR MEASURING PHYSIOLOGICAL PARAMETERS OF A MAMMAL

CROSS REFERENCE TO RELATED APPLICATION

This application claims the benefit of U.S. Provisional Application Ser. No. 61/437,047 filed Jan. 28, 2011, which is hereby incorporated in its entirety herein by reference.

FIELD OF THE DISCLOSURE

The disclosure relates to a non-invasive, ultrasonic monitoring device, worn by a mammal over an area of the mammal's body, which uses ultrasonic technology to evaluate anatomical structures below the mammal's skin in order to determine a physiological status of the mammal.

BACKGROUND OF THE DISCLOSURE

Diagnostic ultrasound is a commonly used technique in medicine and surgery that allows clinicians to see a two dimensional view of a particular body area. This is often used for viewing a fetus in a womb, a gallbladder, or heart valves or chambers. The equipment needed to conduct these types of scans is expensive, requires an experienced operator to perform the scan, and requires the patient to remain at the medical office or hospital during the scan. This technique provides a one-time view of a body area and is not used over a significant period of time for continuously monitoring the body area of interest. In certain situations, it is desirable to continuously or periodically monitor the anatomy of a specific body area of a patient. Some examples of such situations, during which continuous or periodic monitoring is desirable, include: monitoring a diameter of a jugular vein to assess central venous pressure CVP or jugular venous pressure JVP; monitoring a quantity of urine in a bladder; monitoring a quantity of a pleural effusion; or monitoring a quantity of ascites in an abdominal cavity. Many of the current diagnostic ultrasound devices cannot practically monitor the body area on a continuous basis at low cost with minimal inconvenience to the patient. Further, many of the current diagnostic ultrasound devices cannot determine if the monitored area of interest is the intended target area without conducting a scan at considerable expense.

A non-scanning, non-invasive, continuous monitoring, real-time ultrasonic device, and method for its use, is needed to reduce or eliminate one or more problems encountered by one or more of the existing ultrasonic scanning devices.

SUMMARY OF THE DISCLOSURE

In one embodiment, a central venous pressure ultrasonic monitoring device comprises a substrate, a plurality of ultrasonic transducer elements, a computer readable memory medium, a microprocessor, and a power source. The plurality of ultrasonic transducer elements are coupled to the substrate. Each ultrasonic transducer element is separately configured to transmit a signal to a jugular vein of a mammal and to receive an echo return signal from the jugular vein. The computer readable memory medium comprises program instructions. The microprocessor is coupled to the plurality of ultrasonic transducer elements and to the computer readable memory medium for executing the program instructions to determine central venous pressure of the mammal based on a combined analysis of the echo return signals received by the plurality of ultrasonic transducer elements. The power source is coupled to at least one of the plurality of ultrasonic transducer elements, the computer readable memory medium, or the microprocessor for supplying electrical energy.

In another embodiment, a method of monitoring central venous pressure of a mammal is provided. In one step, a central venous pressure ultrasonic monitoring device is positioned against skin of a mammal. In another step, separate signals are transmitted from a plurality of ultrasonic transducer elements of the central venous pressure ultrasonic monitoring device to a jugular vein of the mammal. In an additional step, echo return signals are received, with the plurality of ultrasonic transducer elements, from the jugular vein of the mammal. In yet another step, the central venous pressure of the mammal is determined using a microprocessor to execute program instructions to process a combined analysis of the echo return signals received by the plurality of transducer elements.

In yet another embodiment, an ultrasonic monitoring device comprises a substrate, a plurality of ultrasonic transducer elements, a computer readable memory medium, a microprocessor, and a power source. The plurality of ultrasonic transducer elements are coupled to the substrate. Each ultrasonic transducer element is separately configured to transmit a signal to an area of a mammal and to receive an echo return signal from the area. The computer readable memory medium comprises program instructions. The microprocessor is coupled to the plurality of ultrasonic transducer elements and to the computer readable memory medium for executing the program instructions to determine a physiological parameter of the area based on a combined analysis of the echo return signals received by the plurality of ultrasonic transducer elements. The microprocessor is also configured to determine if the area is an intended target area of the mammal, or to determine whether the ultrasonic monitoring device needs to be relocated to monitor the intended target area of the mammal, based on the combined analysis of the echo return signals received by the plurality of ultrasonic transducer elements. The power source is coupled to at least one of the plurality of ultrasonic transducer elements, the computer readable memory medium, or the microprocessor for supplying electrical energy.

In still another embodiment, a jugular venous pressure ultrasonic monitoring device comprises a substrate, a plurality of ultrasonic transducer elements, a computer readable memory medium, a microprocessor, and a power source. The plurality of ultrasonic transducer elements are coupled to the substrate. Each ultrasonic transducer element is separately configured to transmit a signal to a jugular vein of a mammal, and to receive an echo return signal from the jugular vein. The computer readable memory medium comprises program instructions. The microprocessor is coupled to the plurality of ultrasonic transducer elements and to the computer readable memory medium for executing the program instructions to determine jugular venous pressure of the mammal based on a combined analysis of the echo return signals received by the plurality of ultrasonic transducer elements. The power source is coupled to at least one of the plurality of ultrasonic transducer elements, the computer readable memory medium, or the microprocessor for supplying electrical energy.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. It is noted that FIGS. 1-21, referenced herein, are purely for illustrative purposes and are not to scale.

Figure 1:
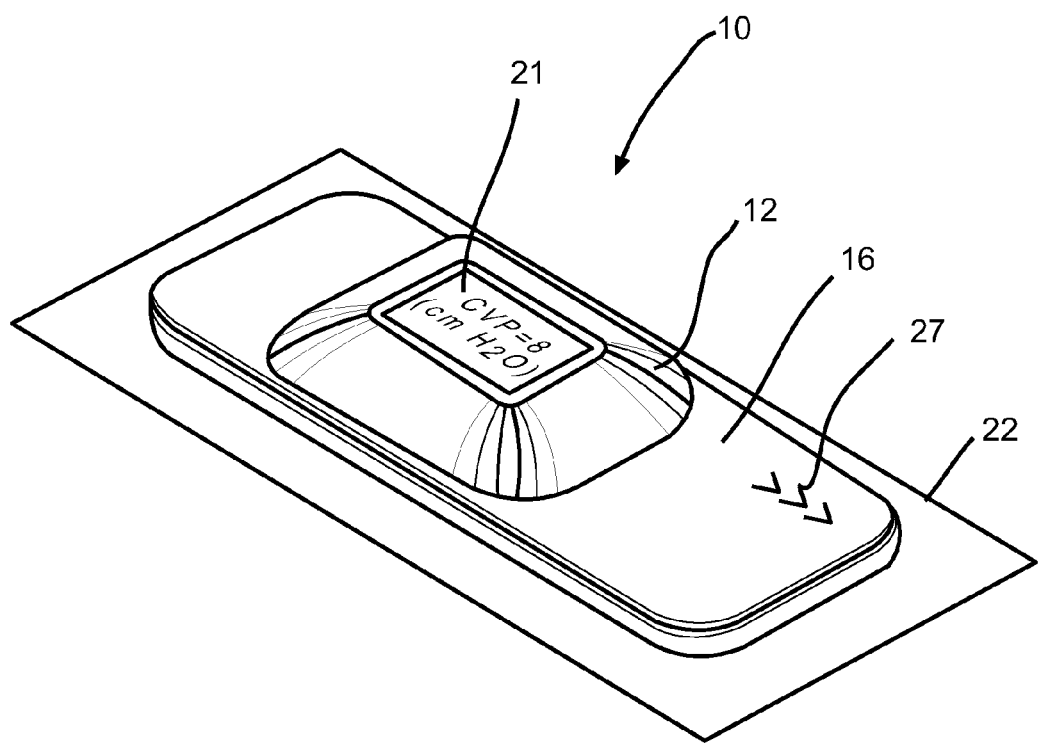
FIG. 1 illustrates a top perspective view of one embodiment of an ultrasonic monitoring device.
Figure 2:
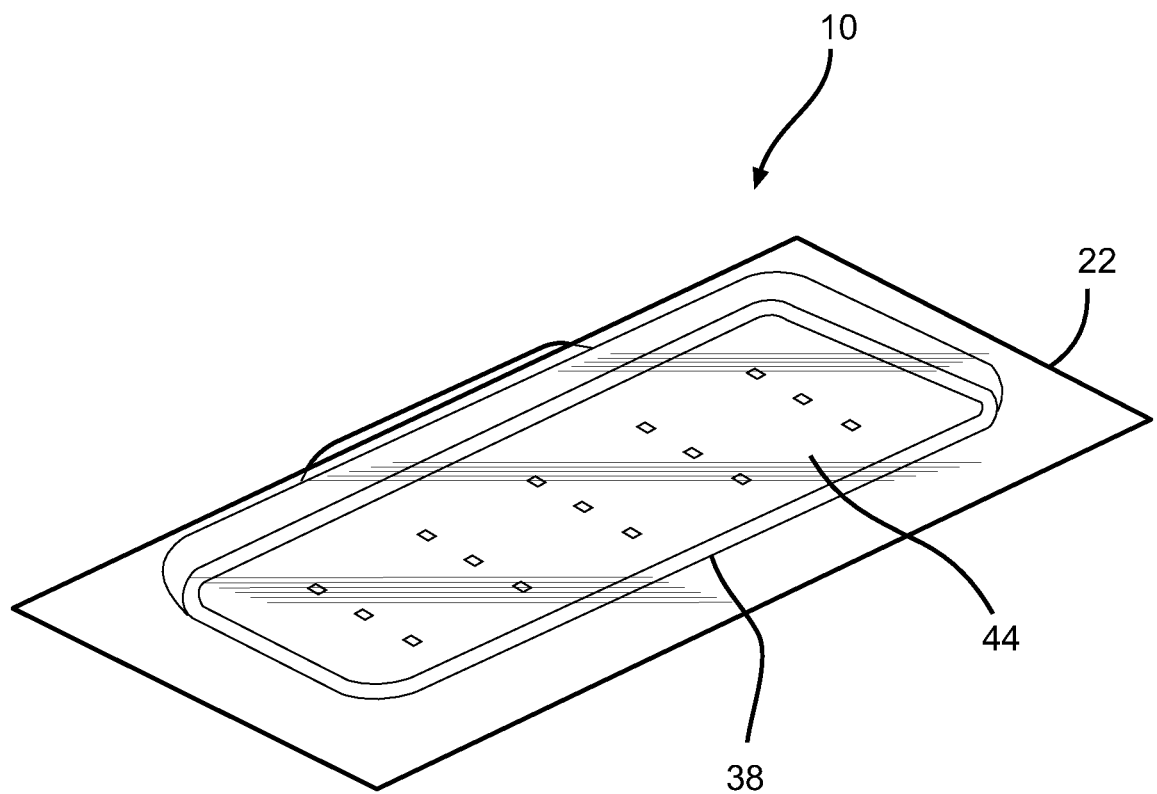
FIG. 2 illustrates a bottom perspective view of the ultrasonic monitoring device of FIG. 1.
Figure 3:
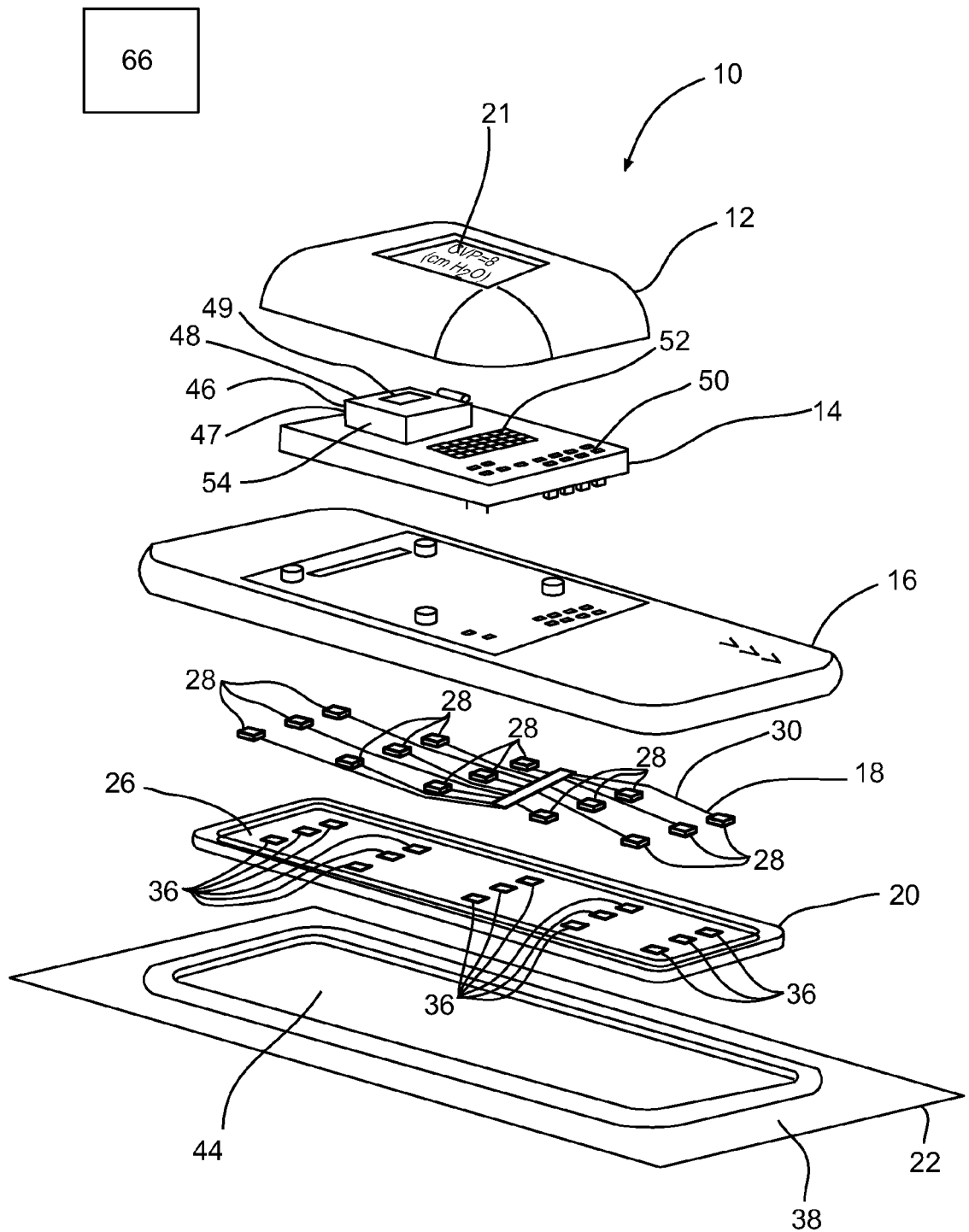
FIG. 3 illustrates an exploded view of the ultrasonic monitoring device of FIGS. 1-2.

FIGS. 1, 2, and 3 illustrate respectively a top perspective view, a bottom perspective view, and an exploded view of one embodiment of an ultrasonic monitoring device 10. The ultrasonic monitoring device 10 is an electronic patch that may be worn by a patient over various areas of the patient's body in order to use ultrasonic technology to evaluate anatomical structures below the patient's skin to determine the physiological status of the patient. As shown in FIG. 3, the ultrasonic monitoring device 10 comprises a first housing surface 12, an electronic system 14, a substrate 16, a sensor system 18, a second housing surface 20, a display 21, and an adhesive, conformable, gel layer 22.

The first housing surface 12 attaches to the substrate 16, through screws or other attachment mechanisms, to house the electronic system 14 within a first cavity (hidden from view) of the first housing surface 12 between the first housing surface 12 and the substrate 16. The first housing surface 12 is rigid and made of a plastic or other type of rigid material. The substrate 16 is made of a semi-rigid, flexible material such as Polyvinyl Chloride (PVC), polycarbonate, a medical plastic, or other type of semi-rigid flexible material. Optionally, an aluminum plate face (not shown) may be placed against the sensor system 18, using an epoxy, to come into contact with an array 28, comprising a plurality of ultrasonic transducer elements of the sensor system 18, and a patient's skin in order to decrease attenuation and increase transmission of the ultrasonic energy. The second housing surface 20 attaches to the substrate 16, through screws or other attachment mechanisms, to house the sensor system 18 within a second cavity 26 of the second housing surface 20. The second housing surface 20 is made of a semi-rigid, flexible material such as a plastic or other type of semi-rigid, flexible material. As shown in FIG. 1, the substrate 16 includes a labeling indicator 27, such as an arrow, which shows the direction, orientation, or positioning in which the ultrasonic monitoring device 10 should be positioned during placement against a surface to be monitored.

The sensor system 18 comprises the array 28 comprising the plurality of ultrasonic transducer elements and a flexible printed circuit board 30 which bridges connectivity between the array 28 of ultrasonic transducer elements and the electronic system 14. The array 28 of ultrasonic transducer elements may comprise of Piezoelectric Crystal (PZT—Lead Zirconate Titanate), or other types of ultrasonic transmitting material. The sensor system 18 electronically connects to the electronic system 14.

The array 28 is arranged so that its ultrasonic transducer elements extend or connect through openings or channels 36 in the second housing surface 20 into contact (direct or indirect) with the adhesive, conformable gel layer 22. The array 28 has five rows and three columns of ultrasonic transducer elements. In other embodiments, the array 28 may comprise five to ten rows of ultrasonic transducer elements, and three to five columns of ultrasonic transducer elements, for a range of fifteen to fifty ultrasonic transducer elements. In further embodiments, the array 28 may have a varying number of rows and columns of ultrasonic transducer elements. Each ultrasonic transducer element of the array 28 has width, length, and depth dimensions of 2 mm by 6 mm by 1 mm. In other embodiments, the ultrasonic transducer elements of the array may have width, length, and depth dimensions which each range up to 20 mm. The ultrasonic transducer elements of the array 28 are 6 mm to 7 mm apart in-between rows and in-between columns. In other embodiments, the ultrasonic transducer elements of the array 28 may be in a range between 5-20 mm apart in-between rows and in-between columns. In still other embodiments, the size and spacing of the ultrasonic transducer elements of the array 28 may vary.

The adhesive, conformable, gel layer 22 comprises a film 38 that adhesively adheres to both the second housing surface 20 and to a surface that the ultrasonic monitoring device 10 is positioned within, for monitoring purposes, in order to minimize movement of the ultrasonic monitoring device 10 during use. The adhesive, conformable, gel layer 22 is flexible and ultrasonically conductive, and may comprise a polymer, or another type of adherent, flexible, ultrasonically conductive material for flexibly and adherently conforming to a mammal's skin. An ultrasound gel 44 is positioned against the adhesive, conformable, gel layer 22 for bridging a gap between the array 28 of ultrasonic transducer elements and the surface being monitored to allow ultrasound energy to transfer from the array 28 of ultrasonic transducer elements to the surface being monitored. The ultrasound gel 44 is made of a compound comprising propylene glycol, carbol 940, phenoxyethanol, and sodium hydroxide. The ultrasound gel 44 is hypoallergenic, greaseless, non-staining, without fragrance, non-irritating, bacteriostatic, non-formaldehyde, non-corrosive, non-acidic, viscous, clear, colorless, and aqueous. The ultrasound gel 44 efficiently transfers, with minimal attenuation, the ultrasound energy between the array 28 of ultrasonic transducer elements and the surface to which the ultrasonic monitoring device 10 is mounted for a period of one to five days. In other embodiments, the ultrasound gel 44 may be made of varying materials, and the monitoring time period upon which the ultrasound gel 44 allows may vary.

Figure 4:
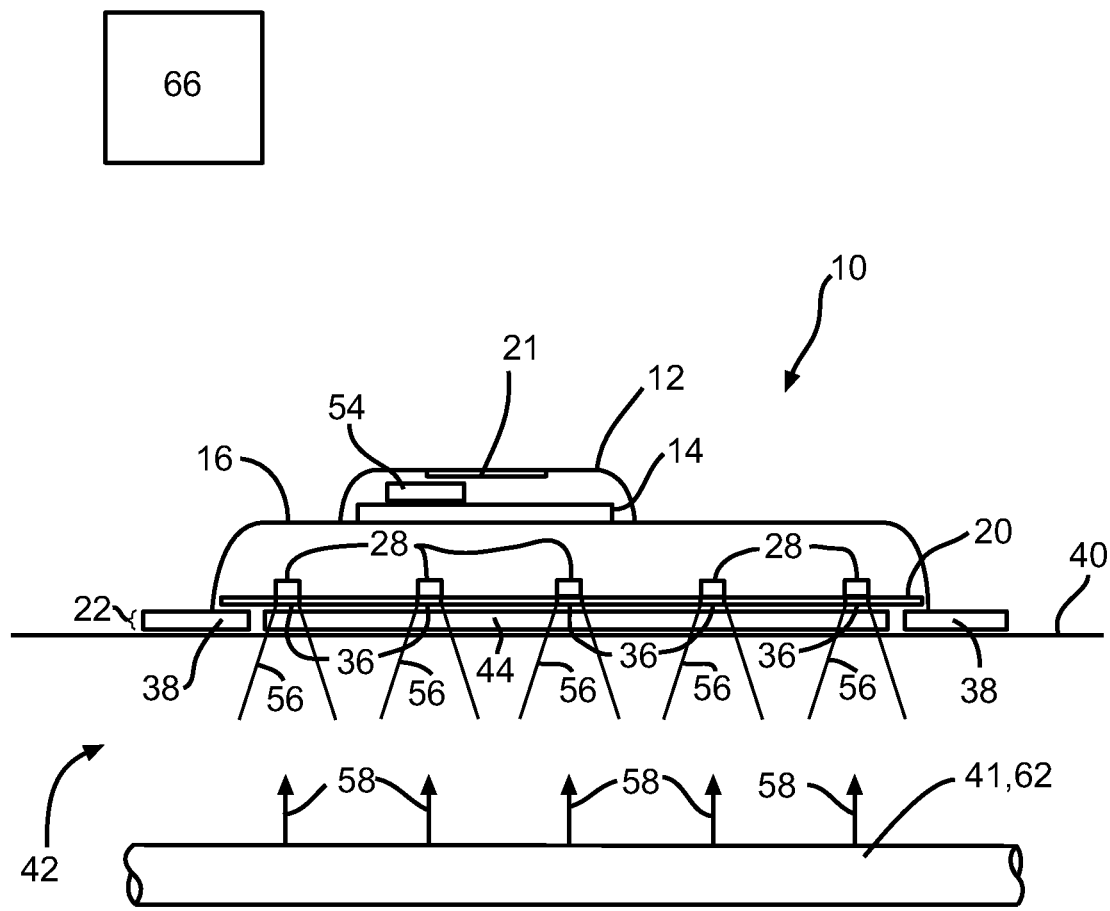
FIG. 4 illustrates an exemplary side view of the ultrasonic monitoring device of FIGS. 1-3 positioned on skin of a mammal to monitor an internal structure of the mammal.

FIG. 4 illustrates an exemplary side view of the ultrasonic monitoring device 10 positioned on skin 40 of a mammal 42 to monitor an internal structure 41 or area of the mammal 42 located beneath the skin 40. The internal structure 41 of the mammal 42 may comprise a jugular vein, a carotid artery, a bladder, a plural effusion, an abdominal cavity, a fetus, a seroma, an edema, lower or upper appendages, or other type of internal structure or area of the mammal 42. The adhesive, conformable gel layer 22 is adhered between the second housing surface 20 and the skin 40, while the ultrasound gel 44 is positioned within the adhesive, conformable gel layer 22 and against array 28 of ultrasonic transducer elements. The ultrasound gel 44 is also positioned between the adhesive, conformable gel layer 22 and the skin 40. Depending on the application of use and the area or surface being monitored, each ultrasonic transducer element of the array 28 is separately configured to transmit a signal 56, towards the internal structure 41 or area of the mammal 42, having a voltage ranging between 10 to 200 Volts, a frequency ranging between 3 to 50 MHz, and to receive a corresponding echo return signal 58, reflected off the internal structure 41, for a time ranging between 1 to 1,000 microseconds. The signal 56 from each ultrasonic transducer element of the array 28 comprises a single beam of ultrasonic energy. The signals 56 transmitted by the ultrasonic transducer elements of the array 28 are intermittent and pulsed. In such manner, the ultrasonic monitoring device 10 monitors the internal structure 41 using a collection of single beams of ultrasonic energy without the use of traditional ultrasonic scanning or imaging methods.

In another embodiment, each ultrasonic transducer element of the array 28 may be separately configured to transmit a signal 56, towards the internal structure 41 of the mammal 42, having a voltage ranging between 50 to 100 Volts, a frequency ranging between 5 to 15 MHz, and to receive a corresponding echo return signal 58, reflected off the internal structure 41, for a time ranging between 1 to 500 microseconds. A time of 200 microseconds corresponds to approximately 15 cm of depth, which will cover most applications of use. In still another embodiment in which the ultrasonic monitoring device 10 is used to monitor central venous pressure CVP, each ultrasonic transducer element of the array 28 is separately configured to transmit a signal 56 having a voltage of approximately 75 Volts, a frequency of approximately 10 MHz, and to receive a corresponding echo return signal 58 for a time ranging between 1 to 50 microseconds. This time range corresponds to a maximum tissue depth of approximately 4 cm. For purposes of this disclosure, the term 'approximately' is defined as within 30%. In other embodiments, the voltage, frequency, and time receipt range of the ultrasonic transducer elements of the array 28 may vary.

As shown in FIG. 3, the electronic system 14 comprises the following connected electronic components for operating the ultrasonic monitoring device 10: a power source 46; an inclinometer 47; a microprocessor 48; amplifiers 50; a wireless connectivity communication device 52; and a computer readable memory medium 54. The power source 46 comprises a battery for powering the electronic system 14. The battery may comprise a flat battery, a rechargeable battery, or another type of battery. In other embodiments, the power source 46 may include any type of power source for powering any number of the components of the electronic system 14.

The microprocessor 48 is connected to the computer readable memory medium 54 and contains or is in contact with a clock 49 for time-stamping. The microprocessor 48 controls the electronic system 14, and further controls, as shown in FIG. 4, the voltage, frequency, and timing of the transmittal of signals 56 transmitted from the array 28 of ultrasonic transducer elements towards the internal structure 41 of the mammal 42, and the corresponding echo return signals 58 reflected off the internal structure 41 of the mammal 42. The amplifiers 50 change the amplitude of the echo return signals 58 received from the array 28 of ultrasonic transducer elements as instructed by the microprocessor 48. The inclinometer 47 determines the inclination state of the mammal 42 relative to (or from) a supine position. The term 'supine position' is defined as a linear position of a mammal 42 lying down horizontally with the mammal's head facing up. The purpose of the inclinometer 47 is to differentiate between the primary positions of a mammal 42 including whether the mammal 42 is sitting upright at a 90 degree angle relative to the supine position, lying in the supine position at a 0 degree angle to the supine position, or resting at some angle between 0 and 90 degrees relative to the supine position. It is not necessary for the inclinometer 47 to be precise, and a resolution/accuracy of 5 degrees is acceptable.

The microprocessor 48 executes program instructions, comprising an algorithm, contained in the computer readable memory medium 54 to determine one or more physiological parameters 62 of the internal structure 41 of the mammal 42 shown in FIG. 4. The microprocessor 48, in conjunction with the computer readable memory medium 54, saves, analyzes, and processes the data generated by the array 28 of ultrasonic transducer elements. The microprocessor 48 uses pattern recognition to analyze and process the echo return signals 58 received by the array 28 of ultrasonic transducer elements. Following the program instructions, the microprocessor 48 processes a combined analysis of the echo return signals 58 received by the array 28 of ultrasonic transducer elements in conjunction with data received from the inclinometer 47 indicating the inclination state of the mammal 42 from (or relative to) a supine position. The ultrasonic monitoring device 10 is configured to be multi-functional to allow monitoring of different areas of the mammal 42. The program instructions are configured to follow different instructions depending on what area, or physiological parameter 62, of the mammal 42 is being monitored. In such manner, the ultrasonic monitoring device 10 may monitor, using different instructions, any number of varying areas, physiological parameters 62, conditions, or internal structures 41 of the mammal 42. The device 10 is also able to use pattern recognition and the initial data gathered to determine what particular area or internal structure 41 it is located near or monitoring. Thereby the device 10 is adapted to automatically select the appropriate program instructions for monitoring the particular area or physiological parameter of interest.

The microprocessor 48 may determine any of the following physiological parameters 62 of the internal structure 41 of the mammal 42, or may determine any of the following relevant information: relative sizes and diameters of an internal structure 41 being monitored, such as at various longitudinal points along a jugular vein, a carotid artery, or another internal structure; a relative blood or fluid level at various locations along or in the internal structure 41, such as along longitudinal locations in a jugular vein, in a carotid artery, or in another internal structure being examined; a central venous pressure CVP in the internal structure 41; a jugular venous pressure JVP in the internal structure 41; a urine quantity in a urinary bladder; a pleural effusion quantity; an ascites quantity in an abdominal cavity; a physiological status of a fetus; a seroma quantity following a mastectomy or breast surgery; a seroma quantity following cosmetic or plastic surgery; an edema quantity in lower or upper appendages; a bladder volume assessment to quantify kidney output; bladder distension due to bladder output obstructions; detection of abnormally narrowed or distended blood vessels; a determination as to whether the internal structure 41 is the intended target area of the mammal 42 based on relative locations of the ultrasonic monitoring device 10 and the internal structure 41 to one or more surfaces, structures, or areas within the mammal 42; a determination as to whether the ultrasonic monitoring device 10 is located in the proper monitoring position to monitor the internal structure 41 allowing the user to reposition the ultrasonic monitoring device 10 into the proper monitoring position if necessary; or other types of physiological parameters 62 of the mammal 42, such the diameter, size, depth, positioning, density, or other information regarding any type of internal structure 41.

For purposes of this disclosure, the term 'mammal' is defined as air-breathing vertebrae animals, including humans. The term 'central venous pressure' or CVP is defined as a pressure of blood in a thoracic vena cava near the right atrium of a heart. The term 'jugular venous pressure' or JVP is defined as an indirectly observed pressure over the venous system in the neck of the mammal 42. The determination of central venous pressure (CVP) or jugular venous pressure (JVP) is helpful in determining whether a mammal 42 has heart or lung disease or an abnormality involving the heart or lungs. The term 'urinary bladder' is defined as an organ that collects urine excreted by the kidneys before disposal by urination. The term 'pleural effusion' is defined as excess fluid that accumulates in the pleura, the fluid-filled space that surrounds the lungs of a mammal 42. The term 'ascites' is defined as an accumulation of fluid in the peritoneal or abdominal cavity. The term 'abdomen' is defined as a part of the mammal 42 between a thorax (chest) and a pelvis. The term 'abdominal cavity' is defined as a region enclosed by the abdomen. The term 'physiological status' is defined as the condition or state of a body or structure. The term 'fetus' is defined as a developing mammal or other viviparous vertebrate after the embryonic stage and before birth. The term 'seroma' is defined as a pocket of serous fluid that may develop in the body following surgery. The term 'edema' is defined as an abnormal accumulation of fluid beneath the skin or in one or more cavities of the body of a mammal 42.

As shown collectively in FIGS. 1-4, the microprocessor 48 stores the determined physiological parameters 62 of the internal structure 41 of the mammal 42 in the computer readable memory medium 54, and either displays the determined physiological parameters 62 on the display 21 located on the first housing 12 of the ultrasonic monitoring device 10, or wirelessly transmits the physiological parameters 62, using the wireless connectivity communication device 52, to a remote device 66 (shown in FIGS. 3 and 4) which displays the transmitted physiological parameters 62 or communicates them to other systems. The display 21 or remote device 66 may comprise an LED display, a Liquid Crystal Display, or other type of display. The wireless connectivity communication device 52 may comprise an antenna, a transmitter/transceiver, or other type of wireless connectivity communication device that uses any type of wireless connection such as a wireless radio frequency connection, Bluetooth, Zigbee, IEEE 802.11a/b/g, or any other type of wireless connection.

The remote device 66 may comprise a remote computer, a hand-held device, or other type of display device such as a docking station cradle, medical pump, vital signs monitor, or doctor or nurse workstation. The display 21 or remote device 66 may visually (and optionally audibly) alert the wearer of the ultrasonic monitoring device 10, another mammal such as a caregiver, or an alert device if the determined physiological parameters 62 are outside of a pre-determined normal range in order to take precautionary, preventative, or surgical responsive measures. The display 21 or remote device 66 may display to the wearer or clinician the detected physiological parameters 62 of the mammal, the normal range of the physiological parameters 62, or an indication as to how far the detected physiological parameters 62 are from the normal range of physiological parameters 62. The display 21 or remote device 66 stores historical physiological parameters 62 to be recalled and displayed anytime. The ultrasonic monitoring device 10 continuously monitors the mammal 42 in real-time for a period ranging between one to five days in order to continuously monitor the physiological parameter 62. In other embodiments, the monitoring time-range may vary. After the monitoring time-range is completed, one or more portions of the ultrasonic monitoring device 10 may be disposed of and never used again. For instance, the entire ultrasonic monitoring device 10 may be intended for one-time use, or some portions of the ultrasonic monitoring device 10 may be used once, such as the adhesive, conformable, gel layer 22, and other portions of the ultrasonic monitoring device 10 may be cleaned or disinfected in a conventional manner and reused.

Figure 5:
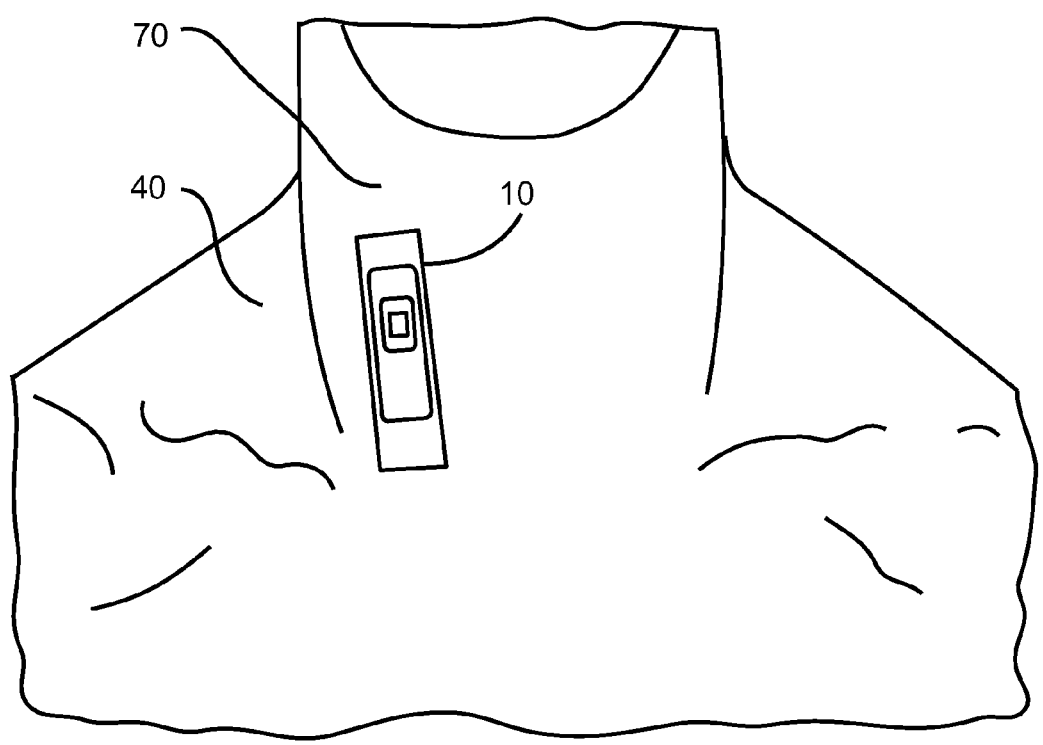
FIG. 5 illustrates a front view of the ultrasonic monitoring device of FIGS. 1-3 positioned against skin of a mammal's neck.
Figure 6:
FIG. 6 illustrates the front view of FIG. 5 with the skin of the mammal's neck removed.

FIG. 5 illustrates a front view of the ultrasonic monitoring device 10 of FIGS. 1-3 positioned against the skin 40 of a mammal's neck 70. FIG. 6 illustrates the front view of FIG. 5 with the skin 40 of the mammal's neck 70 removed. As shown in FIG. 6, the ultrasonic monitoring device 10 is positioned over a jugular vein 72 to monitor the diameter 77 of the jugular vein 72, the blood level in the jugular vein 72, the jugular venous pressure JVP within the jugular vein 72, and the central venous pressure CVP. Normally, blood does not fully fill the jugular vein 72, but blood may fill the jugular vein 72 in various disease states such as during heart failure or during other disease states.

Figure 7:
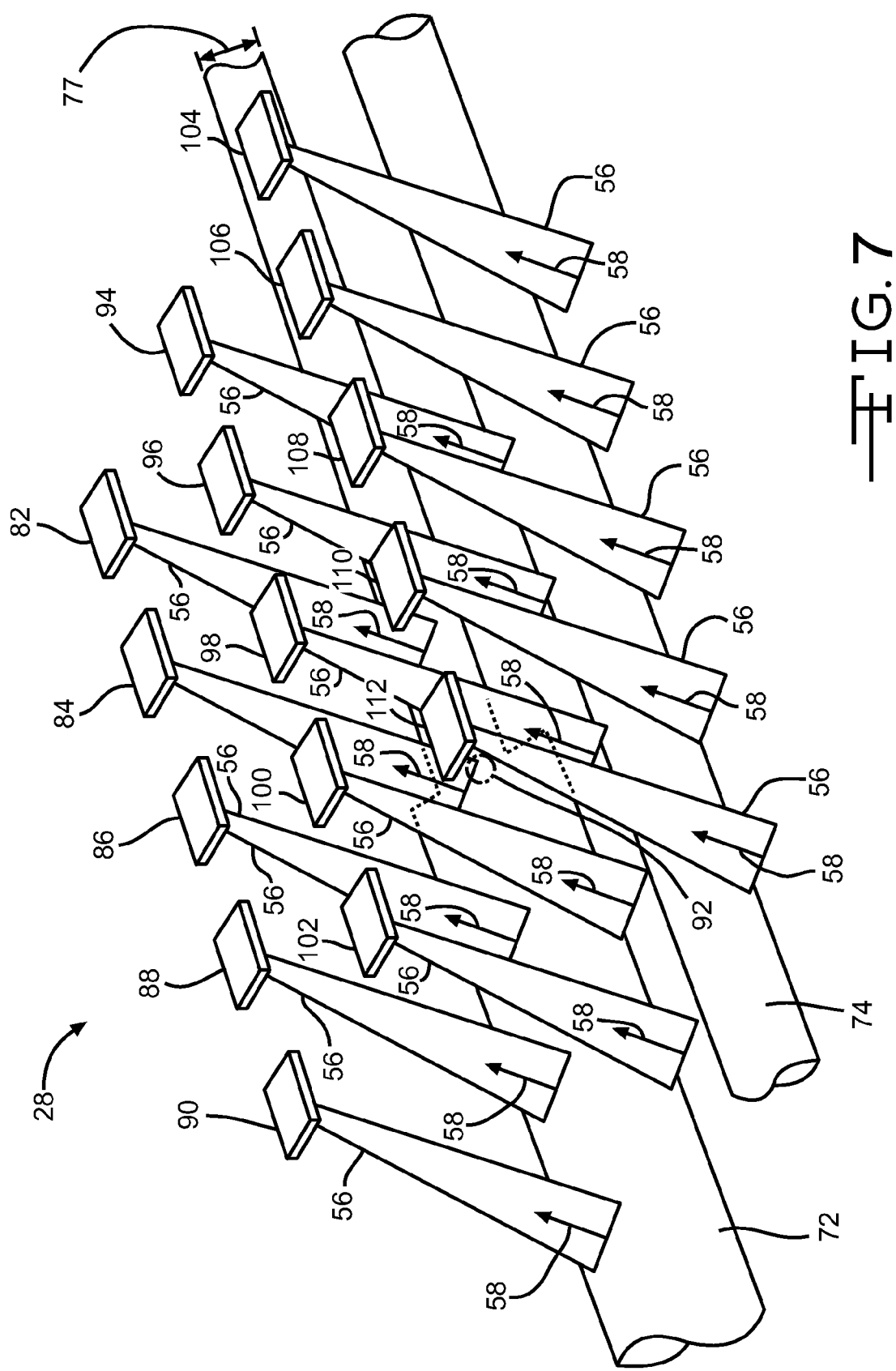
FIG. 7 illustrates an exemplary perspective view showing an array of ultrasonic transducer elements of the ultrasonic monitoring device of FIGS. 1-3, with the other components of the ultrasonic monitoring device removed for illustrative purposes, positioned over a jugular vein and a carotid artery of a mammal's neck.

FIG. 7 illustrates an exemplary perspective view showing the array 28 of fifteen ultrasonic transducer elements of FIGS. 1-3, with the other components of the ultrasonic monitoring device 10 of FIGS. 1-3 removed for illustrative purposes, positioned over a jugular vein 72 and a carotid artery 74 of a mammal's neck. As shown, each ultrasonic transducer of the array 28 of fifteen ultrasonic transducer elements transmits separate signals 56 to the jugular vein 72 or the carotid artery 74. The array 28 of ultrasonic transducer elements receives the corresponding echo return signals 58 reflected off the jugular vein 72 or the carotid artery 74. Each ultrasonic transducer element of the array 28 is separately configured to transmit a signal 56 having a voltage of 75 Volts, a frequency of 10 MHz, and to receive a corresponding echo return signal 58 for a time ranging between 1 to 50 microseconds. This amount of time corresponds to a maximum possible tissue depth of about 4 cm. In other embodiments, the voltage, frequency, and time receipt range of the array 28 of ultrasonic transducer elements may vary in the ranges previously provided depending on the area being monitored.

Each ultrasonic transducer element of the array 28 transduces a small, incomplete section of the jugular vein 72, carotid artery 74, or non-vascular space. Individually, each ultrasonic transducer element of the array 28 gathers incomplete information regarding the state of the jugular vein 72 or carotid artery 74. However, collectively the array 28 of ultrasonic transducer elements gather complete information regarding the corresponding echo return signals 58 for the microprocessor 48 (shown in FIG. 3) to conduct a combined analysis to determine the state of the jugular vein 72 and carotid artery 74. The complete information which is gathered by the array 28 of ultrasonic transducer elements includes: the relative sizes and diameters at various longitudinal points along the jugular vein 72 and carotid artery 74; the relative blood or fluid levels at various longitudinal points along the jugular vein 72 and carotid artery 74; the central venous pressure CVP within the jugular vein 72; the jugular venous pressure JVP within the jugular vein 72; relative positions of the jugular vein 72 and carotid artery 74; and the position of the ultrasonic monitoring device 10 (shown in FIGS. 1-3) relative to the positions of the jugular vein 72 and carotid artery 74 to determine if the ultrasonic monitoring device 10 is properly located for monitoring purposes. In other embodiments, the complete information, which is gathered, may include information regarding the presence, diameter, size, depth, positioning, density, or other information regarding any type of internal structure 41 (shown in FIG. 4) being analyzed by the ultrasonic monitoring device 10.

FIG. 7 shows the array 28 of fifteen ultrasonic transducer elements 82, 84, 86, 88, 90, 94, 96, 98, 100, 102, 104, 106, 108, 110, and 112. As shown in FIG. 7, ultrasonic transducer element 82 receives data from the corresponding echo return signal 58 indicating that the diameter 77 of the jugular vein 72 is in a compressed or collapsed state at that location. Ultrasonic transducer elements 86, 88, and 90 receive data from their corresponding echo return signals 58 indicating that the diameter 77 of the jugular vein 72 is in an expanded state at their locations. Ultrasonic transducer element 84 receives data from its corresponding echo return signal indicating that it is located over a transition location 92 at which the diameter 77 of the jugular vein 72 changes from a compressed or collapsed state to an expanded state. As discussed later, this transition location 92 is needed in order for the microprocessor 48 (of FIG. 3) to be able to determine the jugular venous pressure JVP and the central venous pressure CVP. The transition location 92 shows where fluid or blood is located within the jugular vein 72 relative to the mammal's heart, which assists in determining the jugular venous pressure JVP and the central venous pressure CVP. Ultrasonic transducer elements 82, 84, 86, 88, 90, 94, 96, 98, 100, 102, 104, 106, 108, 110, and 112 collectively receive data from their corresponding echo return signals 58 indicating the relative positions of the jugular vein 72 and the carotid artery 74.

Figure 8:
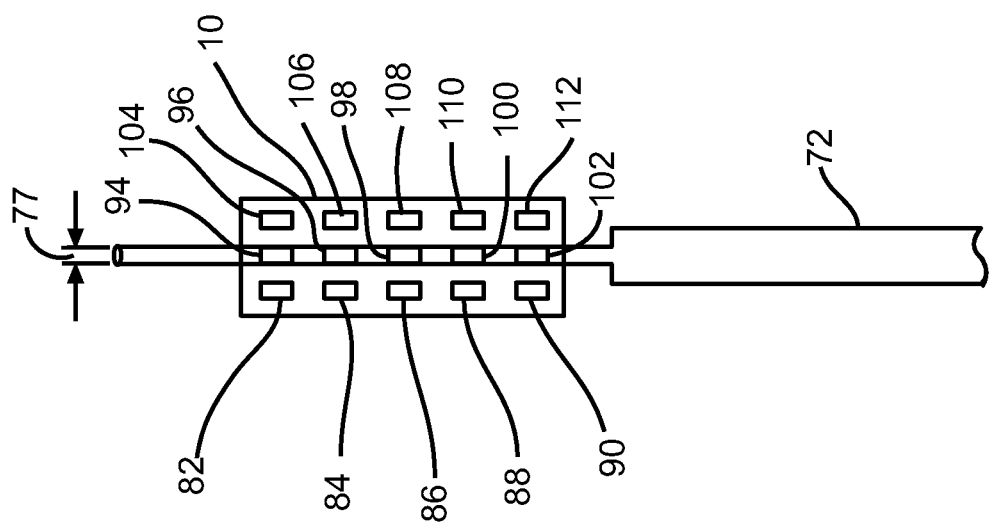
FIG. 8 illustrates an exemplary top view of the ultrasonic monitoring device of FIGS. 1-3 positioned at one longitudinal location relative to a jugular vein.

FIGS. 8-11 illustrate exemplary top views of the ultrasonic monitoring device 10 of FIGS. 1-3 positioned at various longitudinal locations relative to the jugular vein 72. In FIG. 8, the ultrasonic monitoring device 10 is positioned with the ultrasonic transducer elements 94, 96, 98, 100 and 102 located over a diameter 77 of the jugular vein 72 which is in a collapsed state. In this position, the ultrasonic transducer elements 94, 96, 98, 100 and 102 will each gather data indicating that they are located over a diameter 77 of the jugular vein 72 which is in a collapsed state. In this position, the ultrasonic transducer elements 82, 84, 86, 88, 90, 104, 106, 108, 110, and 112 will not detect the jugular vein 72 at all.

With the ultrasonic monitoring device 10 positioned as shown in FIG. 8, the transition location 92 at which the diameter 77 of the jugular vein 72 changes from a collapsed state to an expanded state will not be ascertainable. The data returned from the corresponding echo return signals 58 (shown in FIG. 7) indicates to the microprocessor 48 (shown in FIG. 3) that no transition location 92, at which the diameter 77 of the jugular vein 72 changes from a collapsed state to an expanded state, is detected. In this situation, the microprocessor 48 (shown in FIG. 3) will determine that the jugular venous pressure JVP and the central venous pressure CVP are not detectable at this time and that no numerical calculation of the jugular venous pressure JVP or the central venous pressure CVP is possible. This indicates that the ultrasonic monitoring device 10 is positioned out of alignment with the transition location 92 and needs to be repositioned over the transition location 92 in order to determine the jugular venous pressure JVP and the central venous pressure CVP.

Figure 9:
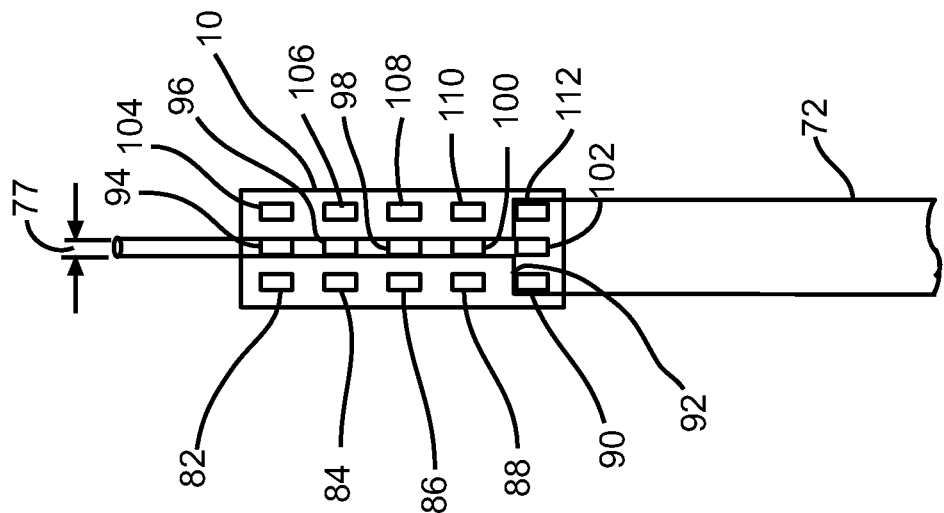
FIG. 9 illustrates the exemplary top view of the ultrasonic monitoring device of FIGS. 1-3 with the ultrasonic monitoring device positioned at another longitudinal location relative to the jugular vein.

In FIG. 9, the ultrasonic monitoring device 10 is positioned so that the ultrasonic transducer elements 94, 96, 98, and 100 are located over a diameter 77 of the jugular vein 72 which is in a collapsed state. In this position, the ultrasonic transducer elements 94, 96, 98, and 100 will each gather data indicating that they are located over a diameter 77 of the jugular vein 72 which is in a collapsed state. Also, in this position, the ultrasonic transducer elements 82, 84, 86, 88, 104, 106, 108, and 110 are located so that they will not detect the jugular vein 72.

In this position, the ultrasonic transducer elements 90, 102, and 112 are located over a diameter 77 of the jugular vein 72 which is in an expanded state, and will gather data indicating this. The collective data gathered by ultrasonic transducer elements 90, 100, 102, and 112 will indicate the location of a transition location 92 at which the diameter 77 of the jugular vein 72 changes from a collapsed state to an expanded state.

With the ultrasonic monitoring device 10 positioned in this location, the data returned from the corresponding echo return signals 58 (shown in FIG. 7) indicates to the microprocessor 48 (shown in FIG. 3) that the ultrasonic monitoring device 10 (shown in FIGS. 1-3) is located in a position in which the transition location 92 has been located allowing the microprocessor 48 (shown in FIGS. 1-3) to determine a numerical value for the jugular venous pressure JVP and the central venous pressure CVP.

Figure 10:
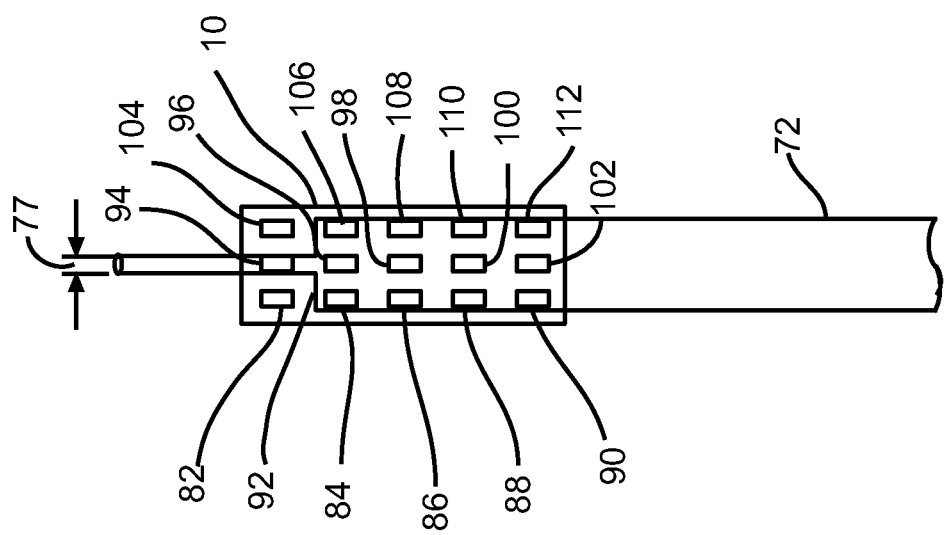
FIG. 10 illustrates the exemplary top view of the ultrasonic monitoring device of FIGS. 1-3 with the ultrasonic monitoring device positioned at still another longitudinal location relative to the jugular vein.

In FIG. 10, the ultrasonic monitoring device 10 is positioned so that the ultrasonic transducer element 94 is located over a diameter 77 of the jugular vein 72 which is in a collapsed state. In this position, the ultrasonic transducer element 94 will gather data indicating that it is located over a diameter 77 of the jugular vein 72 which is in a collapsed state. Also, in this position, the ultrasonic transducer elements 82 and 104 are located so that they will not detect the jugular vein 72 at all. Additionally, in this position, the ultrasonic transducer elements 84, 86, 88, 90, 96, 98, 100, 102, 106, 108, 110, and 112 are located over a diameter 77 of the jugular vein 72 which is in an expanded state, and will gather data indicating this.

The collective data gathered by ultrasonic transducer elements 84, 94, 96, and 106 will indicate the location of a transition location 92 at which the diameter 77 of the jugular vein 72 changes from a collapsed state to an expanded state. With the ultrasonic monitoring device 10 positioned in this location, the data returned from the corresponding echo return signals 58 (shown in FIG. 7) indicates to the microprocessor 48 (shown in FIG. 3) that the ultrasonic monitoring device 10 is located in a position where the transition location 92 has been located allowing the microprocessor 48 (shown in FIG. 3) to determine a numerical value for the jugular venous pressure JVP and the central venous pressure CVP.

Figure 11:
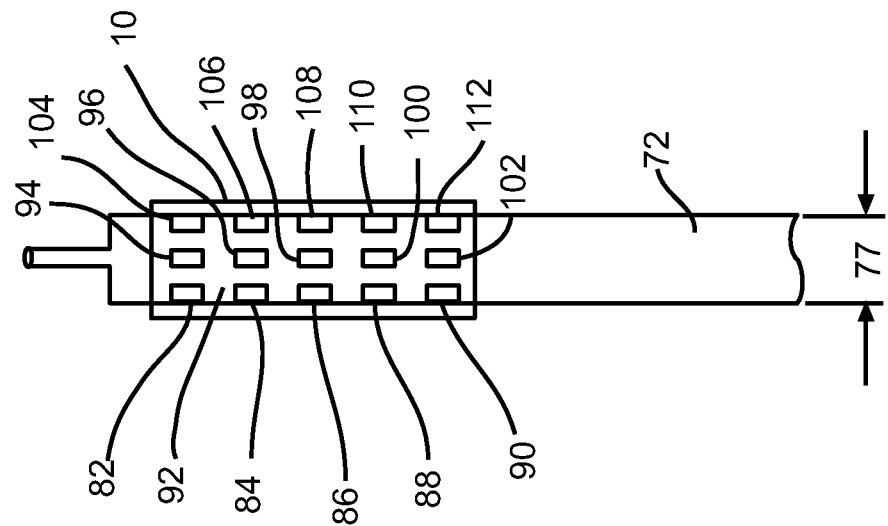
FIG. 11 illustrates the exemplary top view of the ultrasonic monitoring device of FIGS. 1-3 with the ultrasonic monitoring device positioned at yet another longitudinal location relative to the jugular vein.

In FIG. 11, the ultrasonic monitoring device 10 is positioned so that the ultrasonic transducer elements 82, 84, 86, 88, 90, 94, 96, 98, 100, 102, 104, 106, 108, 110 and 112 are located over a diameter 77 of the jugular vein 72 which is in an expanded state. In this position, the ultrasonic transducer elements 82, 84, 86, 88, 90, 94, 96, 98, 100, 102, 104, 106, 108, 110 and 112 will each gather data indicating that they are located over a diameter 77 of the jugular vein 72, which is in an expanded state. With the ultrasonic monitoring device 10 positioned in this location, the transition location 92 at which the diameter 77 of the jugular vein 72 changes from a collapsed state to an expanded state will not be ascertainable.

The data returned from the corresponding echo return signals 58 (shown in FIG. 7) indicates to the microprocessor 48 (shown in FIG. 3) that no transition location 92 (shown in FIG. 7), at which the diameter 77 of the jugular vein 72 changes from a compressed or collapsed state to an expanded state, has been detected. In this situation, the microprocessor 48 (shown in FIG. 3) will determine that the jugular venous pressure JVP and the central venous pressure CVP are out of range of a normal range and that a numerical calculation of the jugular venous pressure JVP and the central venous pressure CVP is not possible. This indicates either that: (1) the ultrasonic monitoring device 10 is positioned in an incorrect position relative to the jugular vein 72 and needs to be moved in order to be positioned over the transition location 92 (shown in FIG. 7) at which the diameter 77 of the jugular vein 72 changes from a collapsed state to an expanded state so that the microprocessor 48 (shown in FIG. 3) can determine the jugular venous pressure JVP and the central venous pressure CVP; or (2) that the central venous pressure is abnormally high and warrants medical intervention.

Figure 12:
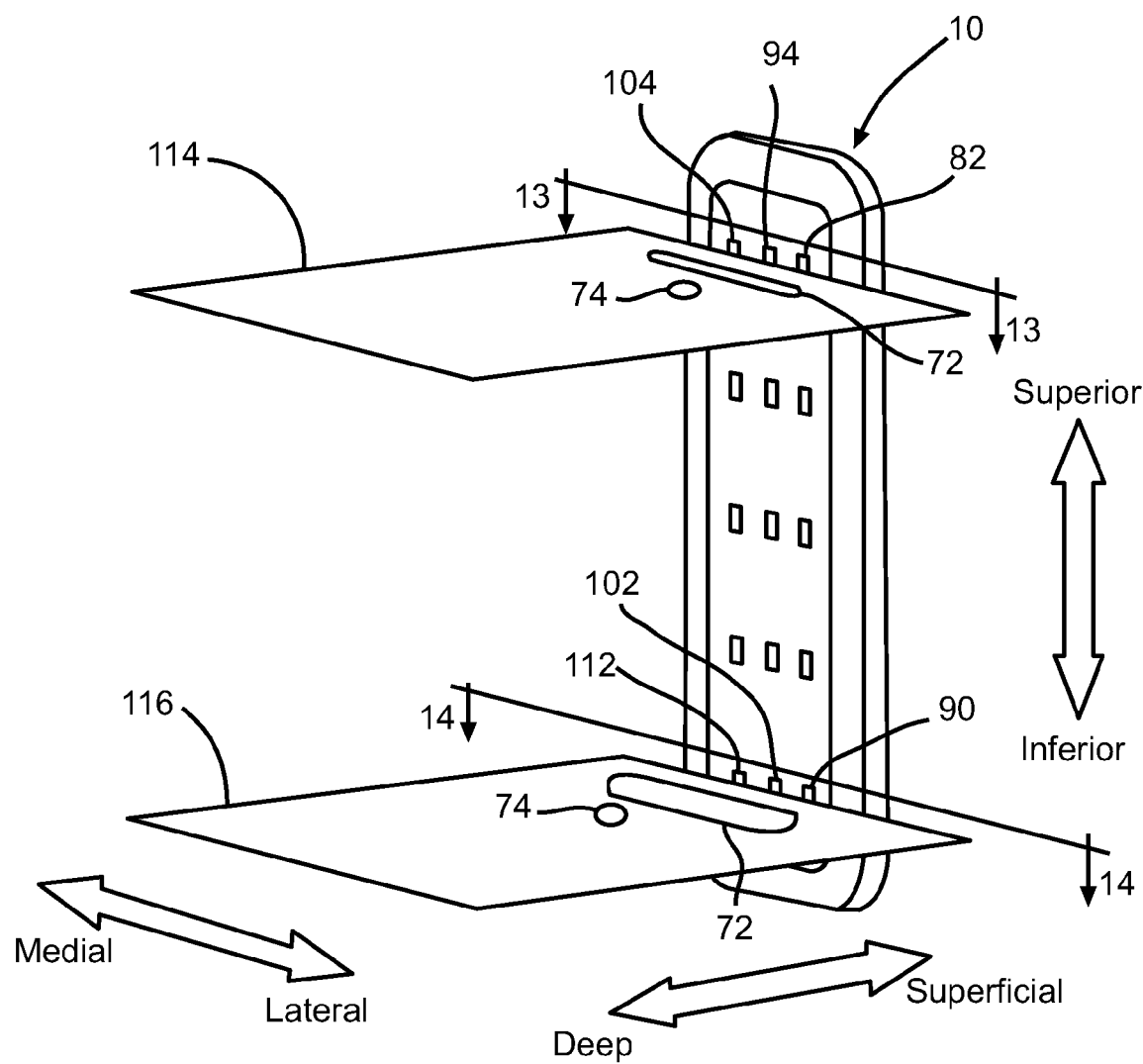
FIG. 12 illustrates an exemplary bottom perspective view of the ultrasonic monitoring device of FIGS. 1-3 positioned over two different two-dimensional ultrasonic images of a right jugular vein and a right carotid artery.
Figure 13:
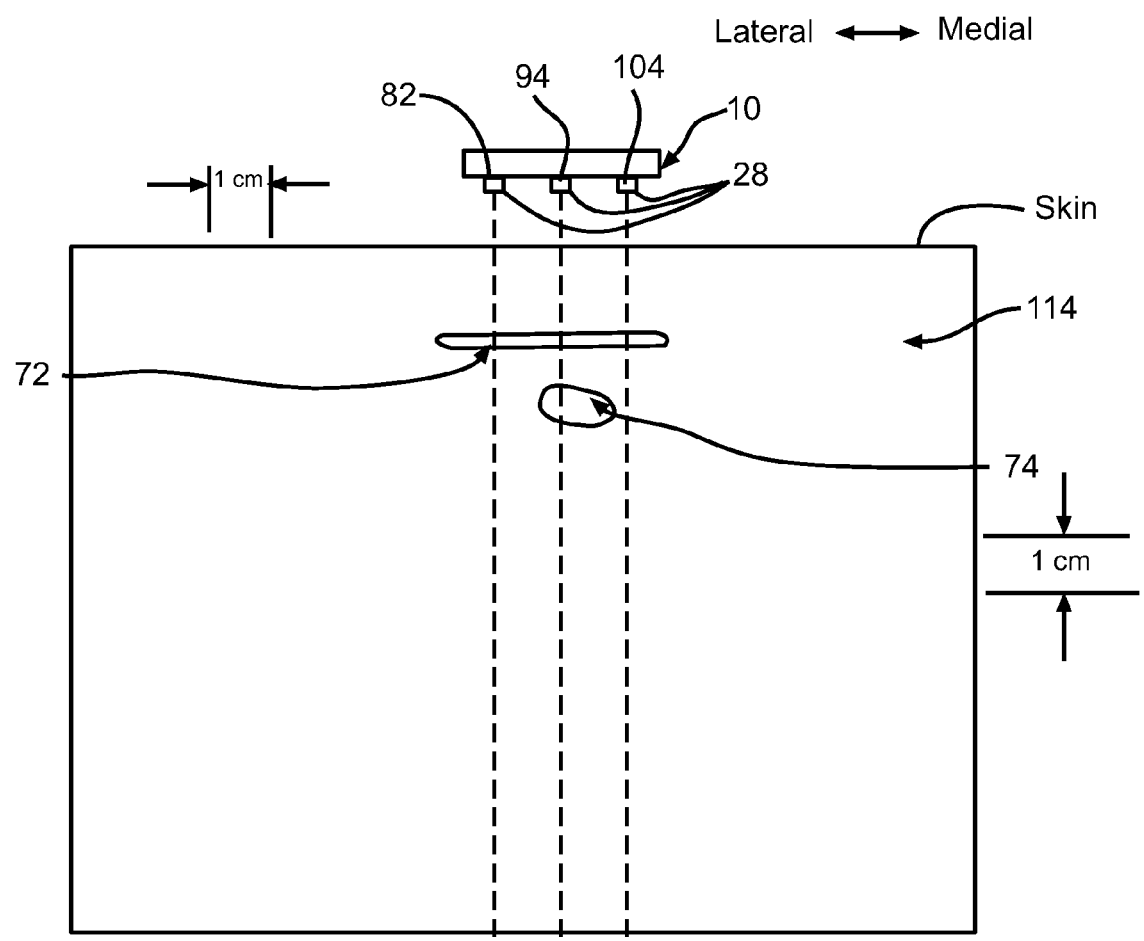
FIG. 13 illustrates a cross-section view through line 13-13 of the ultrasonic monitoring device of FIG. 12 positioned over one of the two-dimensional ultrasonic images of the right jugular vein and the right carotid artery.
Figure 14:
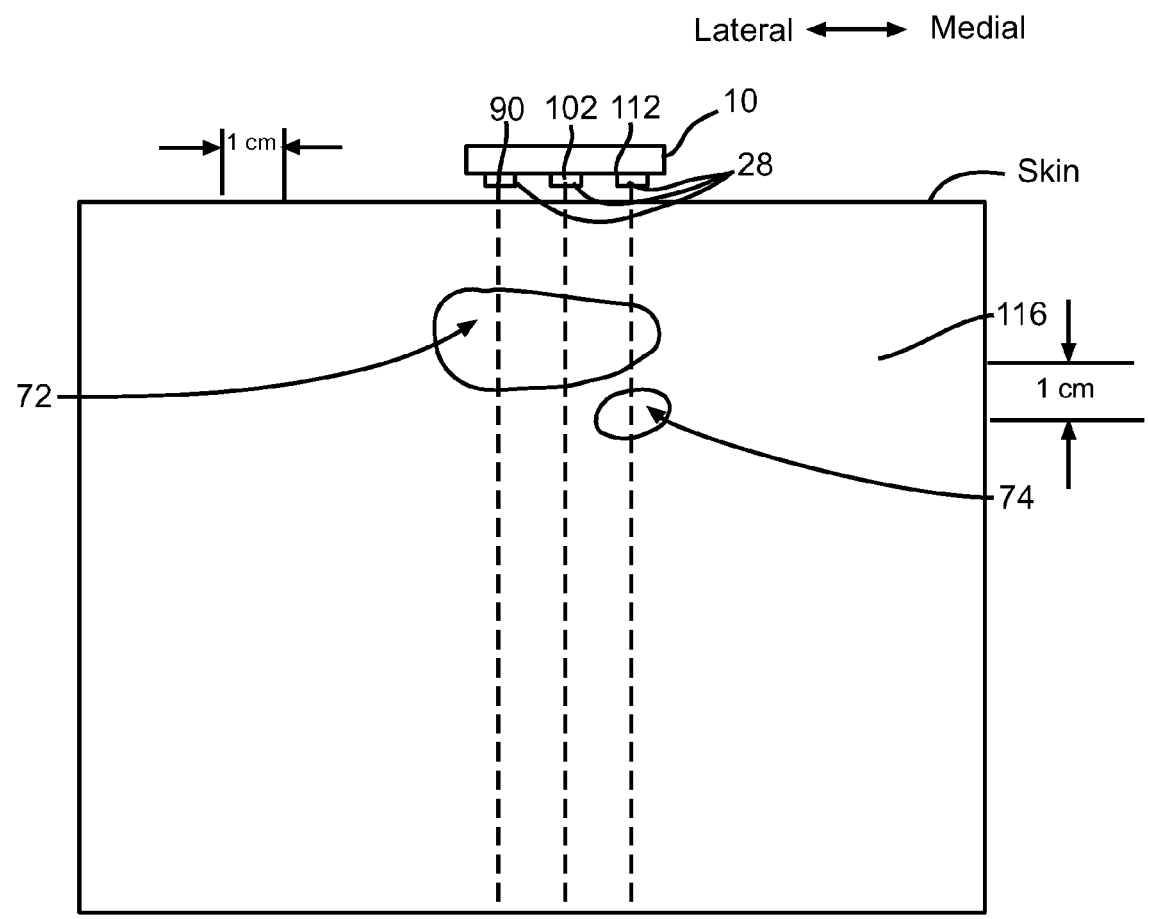
FIG. 14 illustrates a cross-section view through line 14-14 of the ultrasonic monitoring device of FIG. 12 positioned over the second two dimensional ultrasonic image of the right jugular vein and the right carotid artery.

FIGS. 12, 13, and 14 collectively illustrate two dimensional ultrasonic images 114 and 116 of a collapsed jugular vein 72 (shown by ultrasonic image 114 of FIG. 13) and an expanded jugular vein 72 (shown by ultrasonic image 116 of FIG. 14) of the right neck of a mammal along a carotid artery 74 (FIGS. 13 and 14), and the correlation of the two dimensional ultrasonic images 114 and 116 with the placement of the ultrasonic monitoring device 10 over the right neck area of the mammal. More particularly, FIG. 12 illustrates an exemplary bottom perspective view of the ultrasonic monitoring device 10 of FIGS. 1-3 positioned over two different ultrasonic images 114 and 116 of a jugular vein 72 and a carotid artery 74. FIG. 13 illustrates a cross-sectional view through line 13-13 of the ultrasonic monitoring device 10 of FIG. 12 positioned over the first ultrasonic image 114 of the collapsed jugular vein 72 and the carotid artery 74 showing the precise lateral locations of the array 28 of fifteen ultrasonic transducer elements of the ultrasonic monitoring device 10 relative to the collapsed jugular vein 72 and the carotid artery 74. Due to the orientation of the view, only ultrasonic transducer elements 82, 94, and 104 of the first row of the array 28 are viewable with ultrasonic transducer elements 84, 86, 88, 90, 96, 98, 100, 102, 106, 108, 110, and 112 (shown in FIG. 7) of the last four rows of the array 28 being oriented out of the paper and hidden from sight. FIG. 14 illustrates a cross-section view through line 14-14 of the ultrasonic monitoring device 10 of FIG. 12 positioned over the second ultrasonic image 116 of the expanded jugular vein 72 and the carotid artery 74 showing the precise lateral locations of the array 28 of fifteen ultrasonic transducer elements of the ultrasonic monitoring device 10 relative to the expanded jugular vein 72 and the carotid artery 74. Due to the orientation of the cross-section view, only ultrasonic transducer elements 90, 102, and 112 of the last row of the array 28 are viewable with ultrasonic transducer elements 82, 84, 86, 88, 94, 96, 98, 100, 104, 106, 108, and 110 (shown in FIG. 7) of the last four rows of the array 28 being oriented into the paper and hidden from sight. Although the ultrasonic monitoring device 10 does not produce ultrasonic images, FIGS. 13 and 14 are provided to allow the reader, for this particular embodiment for illustrative purposes only, to view the relative lateral positioning of the array 28 of fifteen ultrasonic transducer elements of the ultrasonic monitoring device 10 relative to the collapsed jugular vein 72 (FIG. 13), expanded jugular vein 72 (FIG. 14), and the carotid artery 74 (FIGS. 13 and 14).

Figure 15:
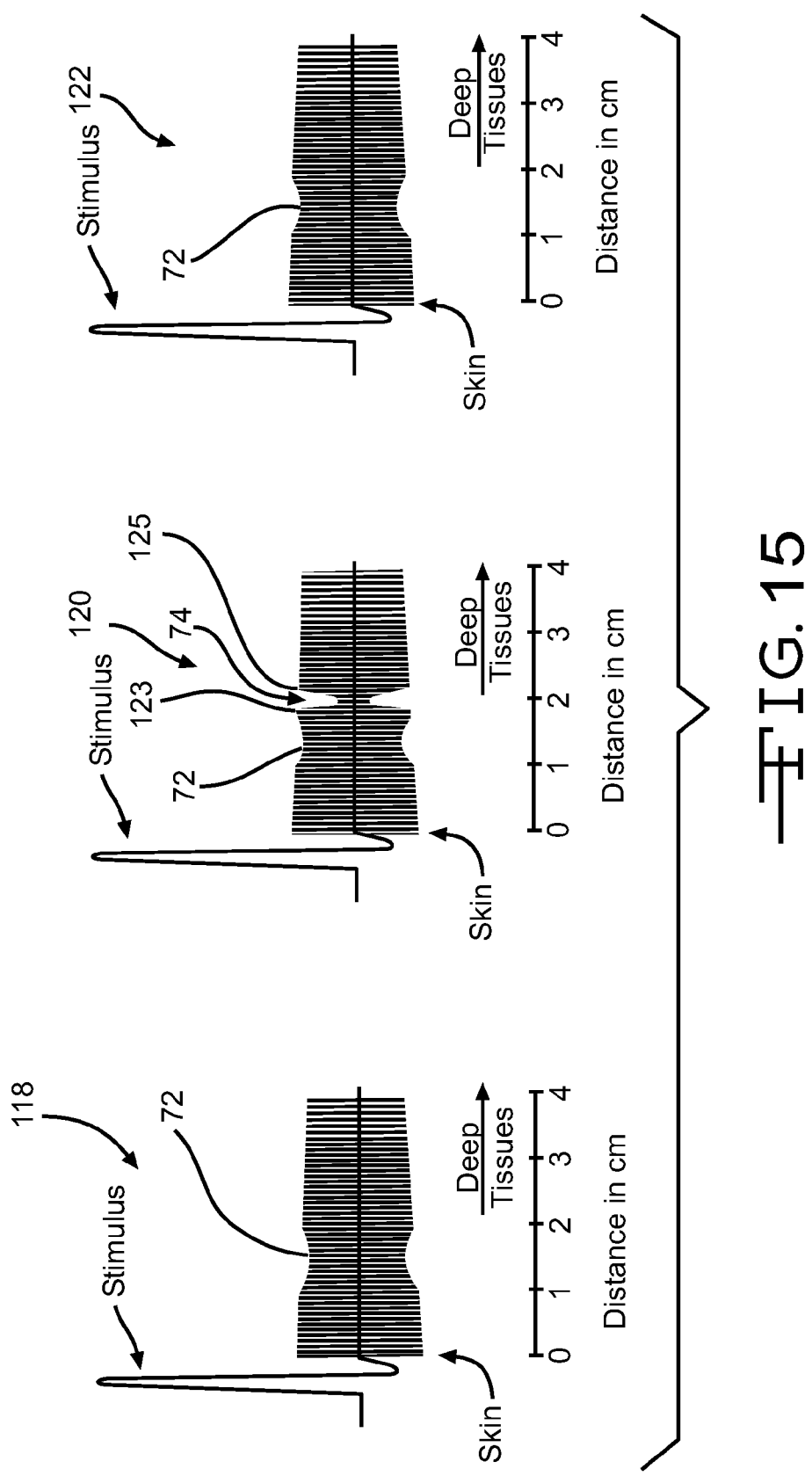
FIG. 15 illustrates three separate echo pulse graphs generated by three corresponding separate ultrasonic transducer elements of the ultrasonic monitoring device of FIG. 13 positioned over the one ultrasonic image depicting a collapsed right jugular vein and right carotid artery.

FIG. 15 illustrates three separate echo pulse graphs 118, 120, and 122 generated by the three corresponding separate ultrasonic transducer elements 82, 94, and 104 shown in FIG. 7 and FIG. 12, for the embodiment shown in FIG. 13 in which the ultrasonic monitoring device 10 is positioned over the first ultrasonic image 114 of the collapsed jugular vein 72 and the carotid artery 74. Echo pulse graph 120 shows the position of the collapsed jugular vein 72 relative to the location of a proximal wall 123 of the carotid artery 74 and a distal wall 125 of the carotid artery 74.

Figure 16:
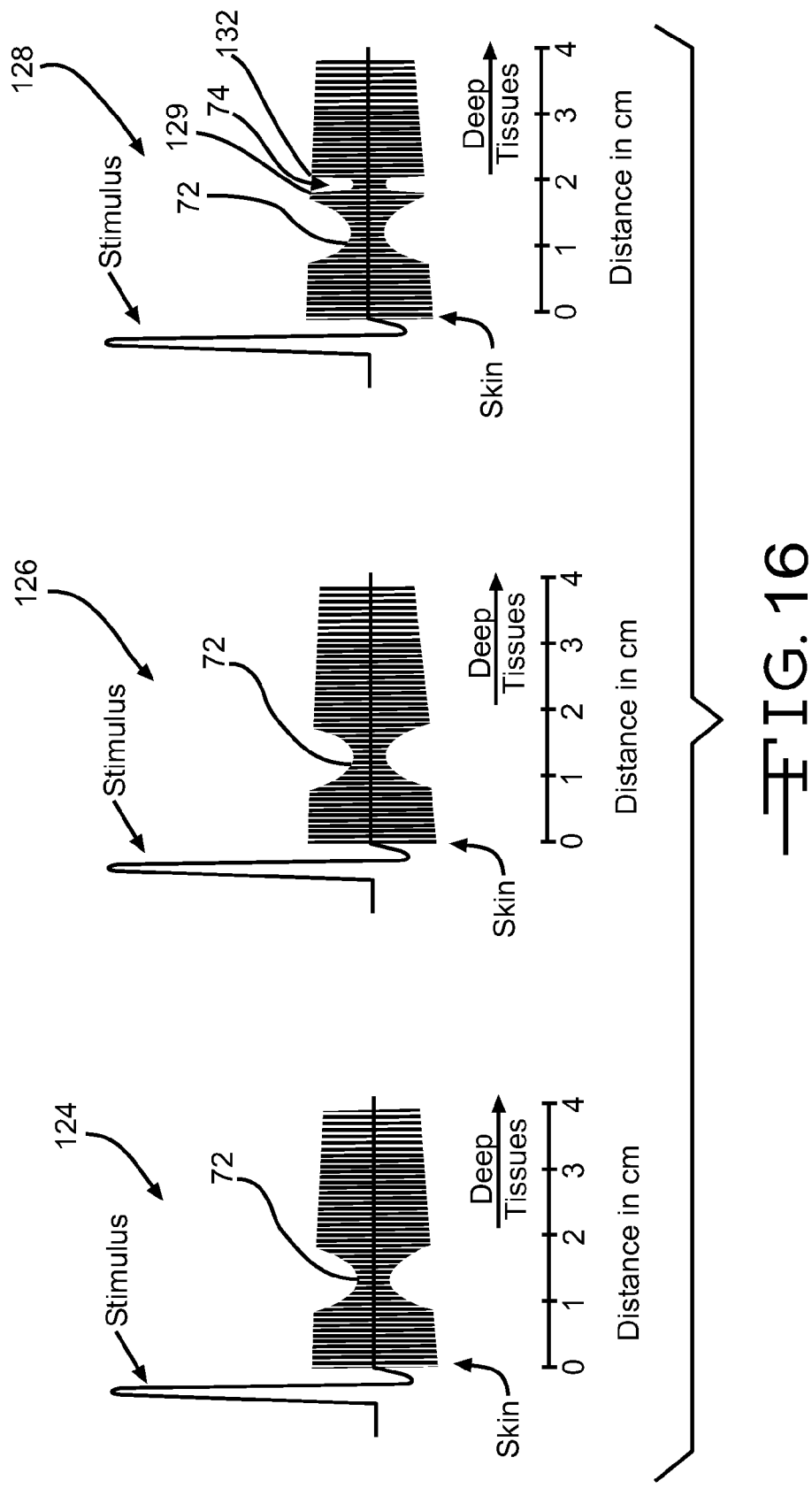
FIG. 16 illustrates three separate echo pulse graphs generated by three corresponding separate ultrasonic transducer elements of the ultrasonic monitoring device of FIG. 14 positioned over the second ultrasonic image depicting an expanded right jugular vein and right carotid artery.

FIG. 16 illustrates three separate echo pulse graphs 124, 126, and 128 generated by the three corresponding separate ultrasonic transducer elements 90, 102, and 112 shown in FIG. 7 and FIG. 12, for the embodiment shown in FIG. 14 in which the ultrasonic monitoring device 10 is positioned over the second ultrasonic image 116 of the expanded jugular vein 72 and the carotid artery 74. Echo pulse graph 128 shows the position of the expanded jugular vein 72 relative to the location of a proximal wall 129 of the carotid artery 74 and a distal wall 132 of the carotid artery 74.

Figure 17:
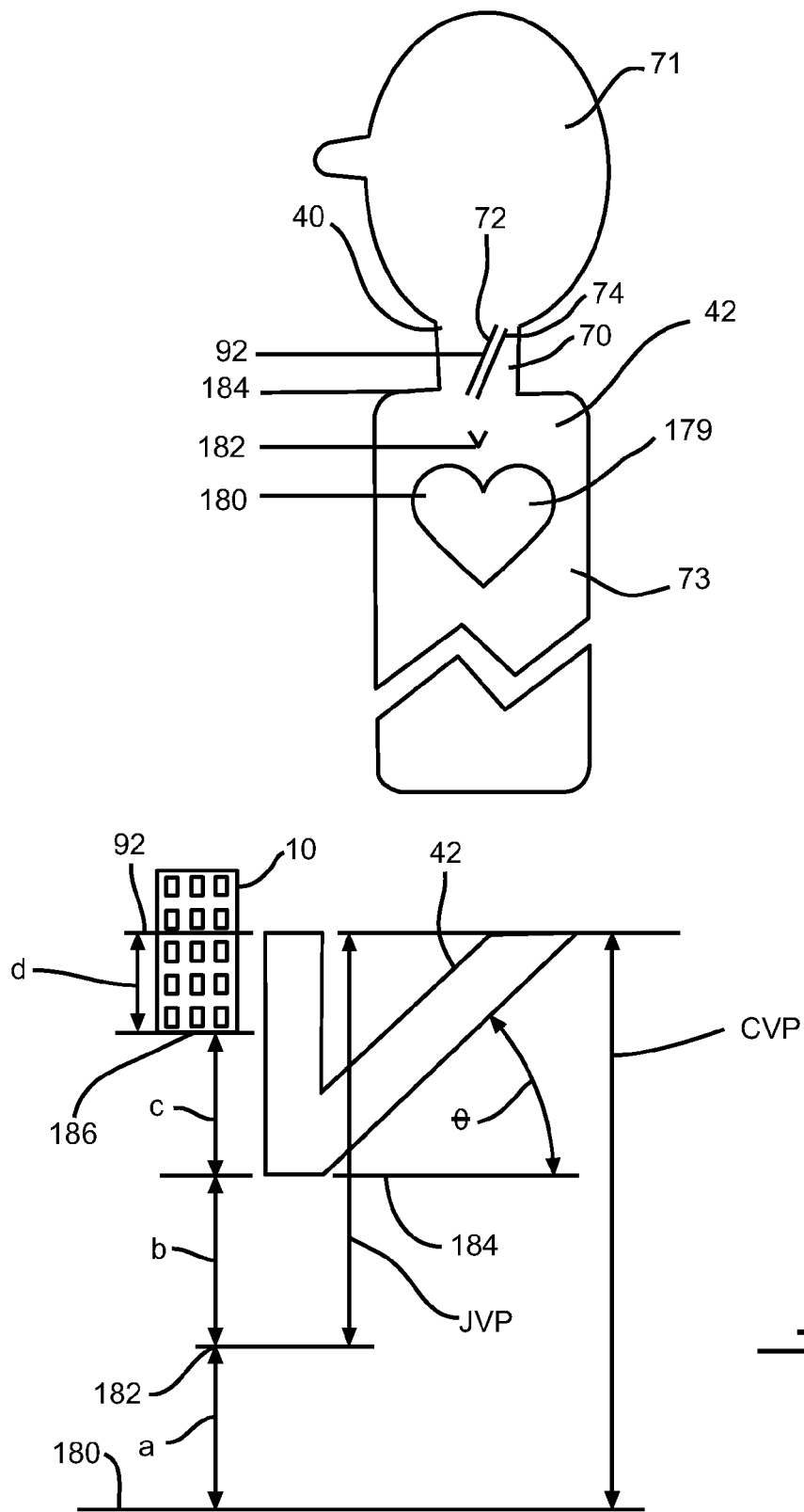
FIG. 17 illustrates a pictorial diagram of a mammal demonstrating how jugular venous pressure JVP and central venous pressure CVP are determined using the ultrasonic monitoring device of FIGS. 1-3.
Figure 18:
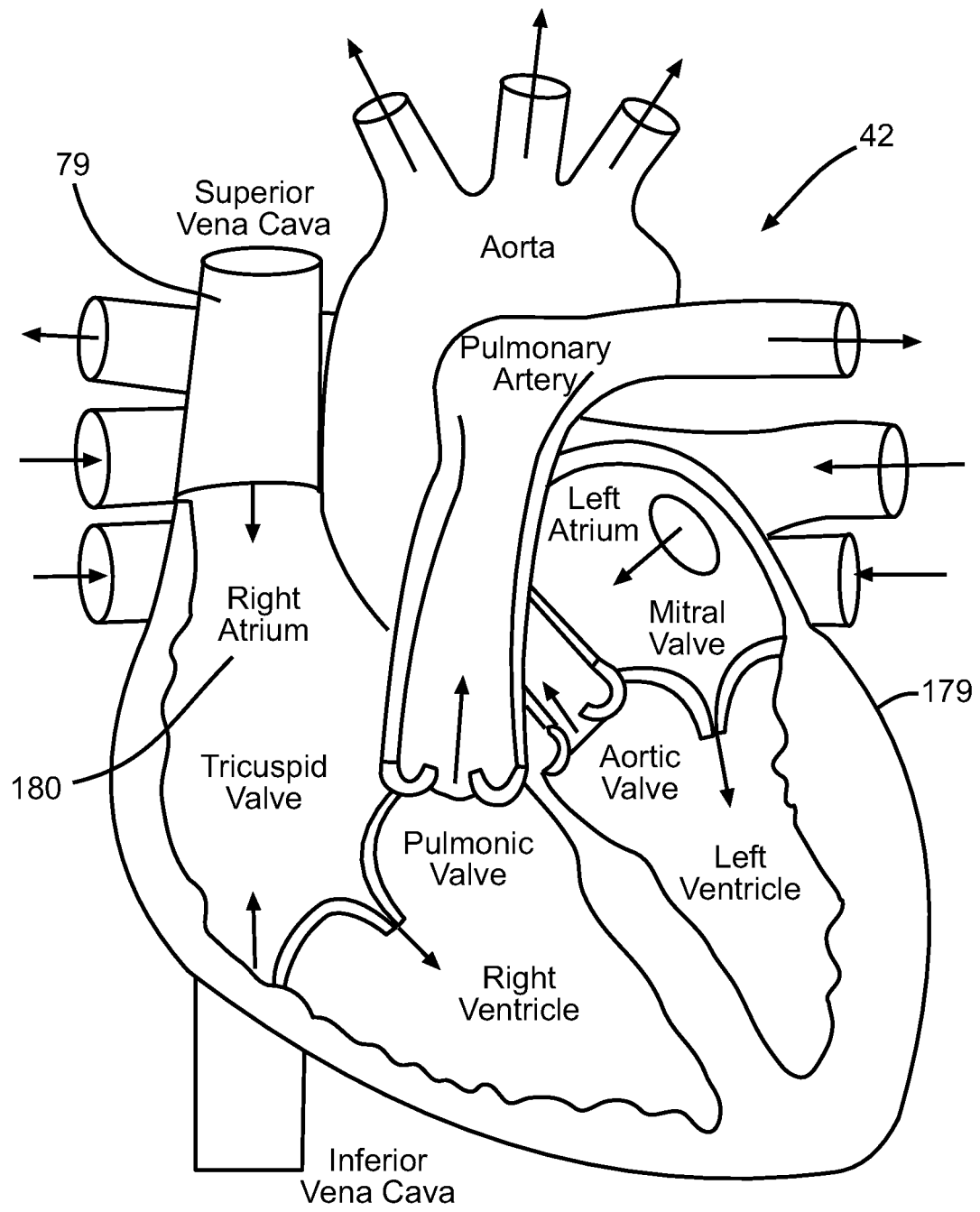
FIG. 18 illustrates a cut-away cross-sectional diagram of a heart of a mammal.

FIG. 17 illustrates a pictorial diagram of a mammal 42 to help demonstrate how the jugular venous pressure JVP and the central venous pressure CVP are determined by the microprocessor 48 of FIG. 3. FIG. 18 illustrates a cut-away cross-sectional diagram of a heart 179 of the mammal 42. As previously discussed, the microprocessor 48 (shown in FIG. 3) executes the program instructions to process the combined analysis of the echo return signals 58 (shown in FIG. 7) received by the array 28 of transducer elements (shown in FIG. 7) using the ultrasonic monitoring device 10 of FIGS. 1-3. As shown in FIGS. 17 and 18 collectively, the mammal 42 has a heart 179, a right atrium 180, a sternal notch 182, a neck 70 having a base 184, a jugular vein 72 having a transition location 92 with fluid in the jugular vein 72, and a carotid artery 74.

The right atrium 180 is one of four chambers in the heart 179 of the mammal 42. The right atrium 180 receives deoxygenated blood and pumps it to other areas of the heart 179 of the mammal 42. The term 'sternal notch' 182 is defined as a v-shaped notch at a top of a sternum (breastbone) of the mammal 42. The term 'neck' 70 is defined a part of the mammal 42 that distinguishes the mammal's head 71 from the mammal's torso 73. The term 'base 184 of the neck 70' is defined as the point where the mammal's torso 73 meets the neck 70 of the mammal 42. The jugular vein 72 brings deoxygenated blood from the mammal's head 71 back to the mammal's heart 179 via the superior vena cava 79. The carotid artery 74 supplies the mammal's head 71 and the mammal's neck 70 with oxygenated blood. The microprocessor 48 (shown in FIG. 3) follows program instructions which use the following algorithm for determining jugular venous pressure JVP=sin θ*(b+c+d). The microprocessor 48 (shown in FIG. 3) further follows program instructions which use the following algorithm for determining central venous pressure CVP=sin θ*(a+b+c+d). In other embodiments, the microprocessor 48 may follow program instructions which use varying algorithms to determine jugular venous pressure JVP, central venous pressure CVP, or other physiological parameters.

For purposes of the algorithms, "θ" is the inclination angle of the mammal 42 from a supine position. The variable "θ" is determined by the inclinometer 47 shown in FIG. 3. The variable "a" is the linear distance from a most superior portion of the right atrium 180 of the mammal 42 to the sternal notch 182 of the mammal 42. The 'most superior portion of the right atrium 180' of the mammal 42 is defined as the point where the superior vena cava 79 enters the right atrium 180. The variable "a" is approximated and is based on the mammal's height, which may be approximated based on the mammal's weight. For instance, "a" is typically approximated to be 4 cm for a 100 pound mammal, 5 cm for a 180 pound mammal, and 6 cm for a 250 pound mammal, assuming the mammal's height to correspond to the mammal's weight. The variable "a" is inputted into the microprocessor 48 (shown in FIG. 3). The variable "b" is the linear distance from the sternal notch 182 of the mammal 42 to the base 184 of the neck 70 of the mammal 42. The variable "b" is determined during a medical examination of the mammal 42 and is inputted into the microprocessor 48 (shown in FIG. 3). In a healthy mammal, the normal distance of the sum of "a" and "b" is 6 cm. The variable "c" is the linear distance from the base 184 of the neck 70 of the mammal 42 to a surface 186 of the ultrasonic monitoring device 10 which is closest to the base 184 of the neck 70 of the mammal 42 as the ultrasonic monitoring device 10 is placed against the skin 40 of the mammal 42 and transmitting the separate signals 56 (as shown in FIGS. 5 and 7). The variable "c" is determined when the ultrasonic monitoring device 10 is positioned against the mammal 42 and is inputted into the microprocessor 48 (shown in FIG. 3). The variable "d" is the linear distance from the surface 186 of the ultrasonic monitoring device 10, which is closest to the base 184 of the neck 70 of the mammal 42 when the ultrasonic monitoring device 10 is placed against the skin 40 of the mammal 42 and transmitting the separate signals 56 (shown in FIG. 7), to the transition location 92 at which the jugular vein 72 of the mammal 42 changes from a collapsed state to an expanded state. The variable "d" is determined as a result of the position of the ultrasonic monitoring device 10 being inputted into the microprocessor 48 (shown in FIG. 3), or being determined by the microprocessor 48, in conjunction with the transition location 92 being determined by the ultrasonic monitoring device 10. In other embodiments, any number of the variables, including the information upon which the variables are based, may be automatically determined by the ultrasonic monitoring device 10.

Figure 19:
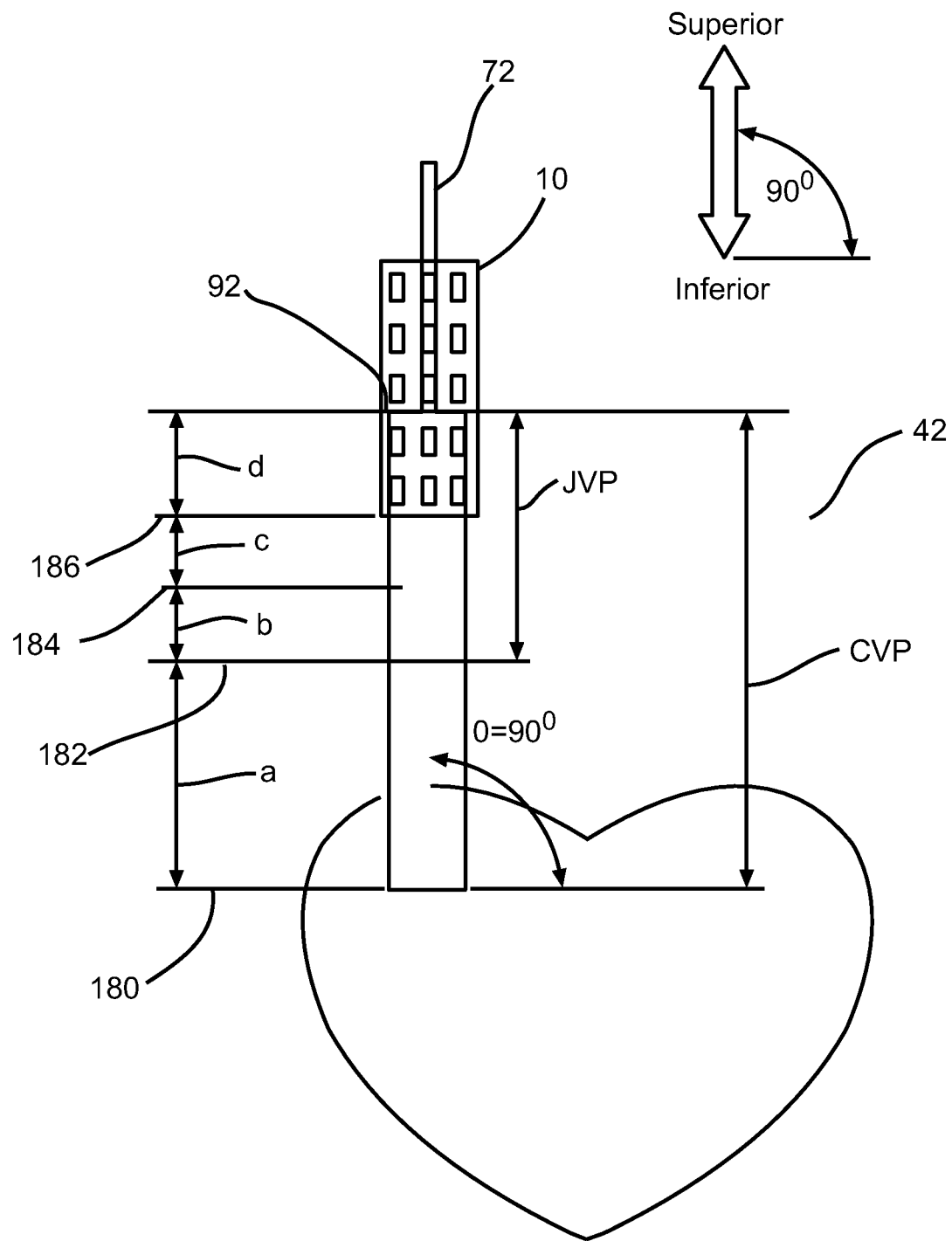
FIG. 19 illustrates a partial cut-away view showing an exemplary embodiment in which the ultrasonic monitoring device of FIGS. 1-3 has been placed onto a mammal positioned at a 90 degree angle (i.e. upright) from the supine position.
Figure 20:
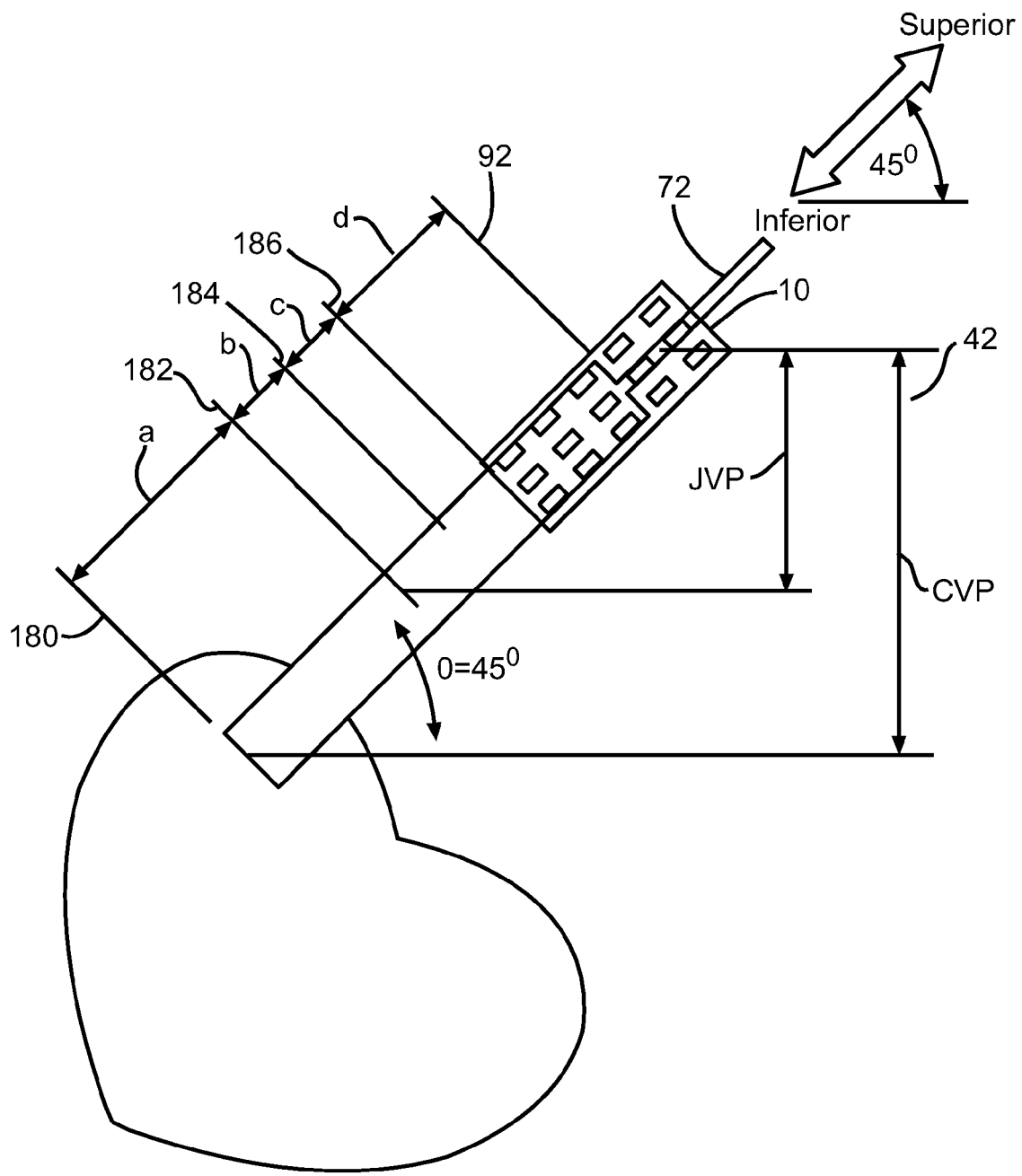
FIG. 20 illustrates a partial cut-away view showing an exemplary embodiment in which the ultrasonic monitoring device of FIGS. 1-3 has been placed onto another mammal positioned at a 45 degree angle from the supine position.

FIGS. 19 and 20 are purely for illustrative purposes to show how the algorithm discussed above with respect to FIG. 17 is applied, and the values of their denoted variables are not to scale with their illustrations. FIG. 19 illustrates a partial cut-away view showing an exemplary embodiment in which the ultrasonic monitoring device 10 has been placed onto a mammal 42 positioned at a 90-degree angle from the supine position (i.e. upright such as sitting or standing straight up at a 90 degree angle from the horizontal). As shown, the ultrasonic monitoring device 10 has been properly located over the transition location 92 at which the jugular vein 72 changes from a collapsed state to an expanded state. For this exemplary embodiment, for purposes of illustrating use of the algorithm discussed in FIG. 17, assume that the variables were determined to be as follows: θ=90 degrees; a=5 cm; b=1 cm; c=1 cm; and d=2 cm. The microprocessor 58 uses data generated by the ultrasonic monitoring device 10 in the algorithm discussed in FIG. 17 to determine that the jugular venous pressure JVP=sin θ*(b+c+d)=sin 90 degrees*(1+1+2)=1*(4)=4 cmH$_2$O, and to determine that the central venous pressure CVP=sin θ*(a+b+c+d)=sin 90 degrees*(5+1+1+2)=1*(9)=9 cmH$_2$O. A normal central venous pressure CVP for a healthy adult is known to be in a range of between 2 to 9 cmH$_2$O. As a result, use of the ultrasonic monitoring device 10 demonstrates that in this exemplary embodiment, the mammal 42 has a central venous pressure CVP that falls within the normal range.

FIG. 20 illustrates a partial cut-away view showing an exemplary embodiment in which the ultrasonic monitoring device 10 has been placed onto the same mammal 42 as in FIG. 19, having the same central venous pressure CVP, positioned at a 45 degree angle from the supine position (i.e. sitting at a 45 degree angle relative to the horizontal). As shown, the ultrasonic monitoring device 10 has been properly located over the transition location 92 at which the jugular vein 72 changes from a collapsed state to an expanded state. For this exemplary embodiment, for purposes of illustrating use of the algorithm discussed in FIG. 17, assume that the variables were determined to be as follows: θ=45 degrees; a=5 cm; b=1 cm; c=1 cm; and d=5.73 cm. The microprocessor 58 of FIG. 3 uses data generated by the ultrasonic monitoring device 10 in the algorithm discussed in FIG. 17 to determine that the jugular venous pressure JVP=sin θ*(b+c+d)=sin 45 degrees*(1+1+5.73)=0.707*(7.73)=5.47 cmH$_2$O, and to determine that the central venous pressure CVP=sin θ*(a+b+c+d)=sin 45 degrees*(5+1+1+5.73)=0.707*(12.73)=9.00 cmH$_2$O. This illustrates that the algorithm generates the same central venous pressure CVP for the mammal 42, when the ultrasonic monitoring device 10 is properly placed and can locate a transition location 92, regardless of whether the mammal 42 is in the full upright position of FIG. 19 or in the reclined position of FIG. 20.

In the event that the ultrasonic monitoring device 10 of FIGS. 1-3 is unable to locate a transition location 92 using its array 28 of transducer elements in a mammal 42 having an abnormally high central venous pressure CVP, the algorithm will detect that the jugular vein 72 is fully expanded along the entire length of the ultrasonic monitoring device 10. This could occur with the mammal 42 in a fully upright position or in a reclined position at any degree from the full upright position. In the case of the mammal 42 being relatively upright (i.e. reclining 0 to 30 degrees from the upright position), and the ultrasonic monitoring device 10 detecting a fully expanded jugular vein 72 along the entire length of the ultrasonic monitoring device 10, the ultrasonic monitoring device 10 will periodically report a "CVP over-range" condition. In the case of the mammal 42 being in a reclined position (i.e. reclining more than 30 degrees from the upright position), and the ultrasonic monitoring device 10 detecting a fully expanded jugular vein 72 along the entire length of the ultrasonic monitoring device 10, the ultrasonic monitoring device 10 will periodically report a "CVP Over-range/Last Upright CVP=X", with X being the last known central venous pressure CVP, providing that the ultrasonic monitoring device 10 previously detected either: (1) a central venous pressure CVP measurement from a detectable transition location 92; or (2) a "CVP under range" condition in which the ultrasonic monitoring device 10 measured a collapsed jugular vein 92 along the entire length of the ultrasonic monitoring device 10. A typical example of a "CVP Over-range" condition is when the mammal 42 is sleeping in a fully supine position. In this situation, the ultrasonic monitoring device 10 cannot measure a central venous pressure CVP because the jugular vein 92 is in an expanded state along the entire length of the ultrasonic monitoring device 10.

In the event that the ultrasonic monitoring device 10 of FIGS. 1-3 is unable to locate a transition location 92 using its array 28 of transducer elements in a mammal 42 having a low central venous pressure CVP, the ultrasonic monitoring device 10 will periodically report a "CVP under range" condition. This could occur in a mammal 42 who has recovered from a fluid overload state, in an euvolemic mammal 42, or in a dehydrated mammal 42.

Figure 21:
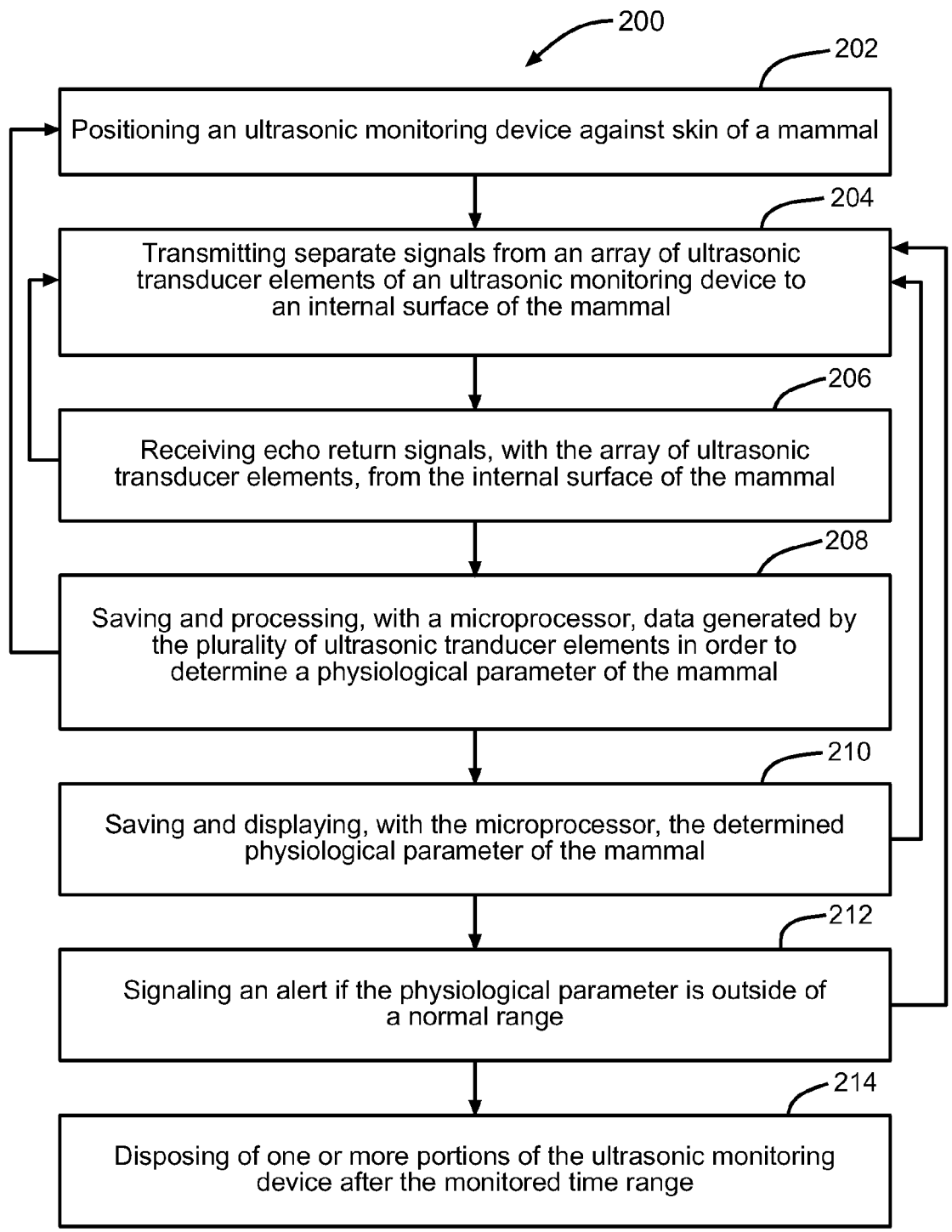
FIG. 21 illustrates a flowchart showing steps of one embodiment of a method for ultrasonically monitoring an internal structure of a mammal.

FIG. 21 illustrates a flowchart showing steps of one embodiment of a method 200 for continuously and non-invasively ultrasonically monitoring an internal structure 41 of a mammal 42 over a period of time in order to determine a physiological parameter 62 of the internal structure 41 without using any mechanical or electrical scanning techniques, such as those used in traditional diagnostic ultrasonic imaging, to acquire information about the internal structure 41. The method 200 may be followed to monitor any of the following physiological parameters 62 or to determine any of the following information: monitor relative sizes and diameters at various longitudinal points along an internal structure 41, such as a jugular vein 72 or other type of internal structure 41; monitor the relative blood or fluid level at various longitudinal points in the internal structure 41; monitor a central venous pressure CVP; monitor a jugular venous pressure JVP; monitor a urine quantity in a urinary bladder; monitor a pleural effusion quantity; monitor an ascites quantity in an abdominal cavity; monitor a physiological status of a fetus; monitor a seroma following a mastectomy or breast surgery; monitor a seroma following cosmetic or plastic surgery; monitor edema of lower or upper appendages; monitor a bladder volume assessment to quantify kidney output; monitor a bladder distension due to bladder output obstructions; monitor or detect abnormally narrowed or distended blood vessels; monitor other types of physiological parameters 62 of the mammal 42; make a determination as to whether the internal structure 41 is an intended target area of the mammal 42 based on relative locations of the ultrasonic monitoring device 10 and the internal structure 41 to one or more surfaces, structures, or areas within the mammal 42; determine whether the ultrasonic monitoring device 10 is located in the proper monitoring position for monitoring the internal structure 41 allowing the user to reposition the ultrasonic monitoring device 10 into the proper monitoring position if needed; or determine other types of physiological parameters 62 of the mammal 42, such as the presence, diameter, size, depth, positioning, density, or other information regarding any type of internal structure 41.

In step 202, an ultrasonic monitoring device 10 is placed against the skin 40 of the mammal 42. In step 204, separate signals 56 are transmitted from the array 28 of ultrasonic transducer elements of the ultrasonic monitoring device 10 to an internal structure 41 of the mammal 42. Depending on the application of use and the area or surface being monitored, each ultrasonic transducer element of the array 28 may be separately configured to transmit a signal 56, towards the internal structure 41 or area of the mammal 42, having a voltage ranging between 10 to 200 Volts, a frequency ranging between 3 to 50 MHz, and to receive a corresponding echo return signal 58, reflected off the internal structure 41, for a time ranging between 1 to 1,000 microseconds. In another embodiment, each ultrasonic transducer element of the array 28 may be separately configured to transmit a signal 56, towards the internal structure 41 of the mammal 42, having a voltage ranging between 50 to 100 Volts, a frequency ranging between 5 to 15 MHz, and to receive a corresponding echo return signal 58, reflected off the internal structure 41, for a time ranging between 1 to 500 microseconds. In still another embodiment in which the ultrasonic monitoring device 10 is used to monitor central venous pressure CVP, each ultrasonic transducer element of the array 28 is separately configured to transmit a signal 56 having a voltage of approximately 75 Volts, a frequency of approximately 10 MHz, and to receive a corresponding echo return signal 58 for a time ranging between 1 to 50 microseconds. This amount of time corresponds to a maximum possible tissue depth of about 4 cm.

In other embodiments, the voltage, frequency, and time receipt range of the ultrasonic transducer elements of the array 28 may vary in the ranges previously provided depending on the area being monitored. The time range used determines the maximum possible tissue depth that the ultrasonic monitoring device 10 monitors. The internal structure 41 of the mammal 42 being monitored may comprise a jugular vein, a carotid artery, a bladder, a plural effusion, an abdominal cavity, a fetus, a seroma, edema of the lower or upper appendages, or other type of internal structure or area of the mammal 42.

In step 206, echo return signals 58 are received, with the array 28 of ultrasonic transducer elements, from the internal structure 41 of the mammal 42. Only one of the ultrasonic transducer elements of the array 28 is energized at a time and its corresponding echo return signal 58 is acquisitioned and stored before a successive ultrasonic transducer element of the array 28 is energized. Steps 204 and 206 are repeated until all of the ultrasonic transducer elements of the array 28 have received their separate corresponding echo return signals 58. In step 208, a microprocessor 48 saves, analyzes, and processes the data generated by the plurality of ultrasonic transducer elements of the array 28, and uses the data to determine a physiological parameter 62 of the mammal 42 by executing program instructions to process a combined analysis of the echo return signals 58 received by the plurality of transducer elements of the array 28. The microprocessor 48 uses pattern recognition to analyze and process the echo return signals 58 received by the plurality of ultrasonic transducer elements of the array 28.

During step 208, the microprocessor 48 may determine whether the internal structure 41 being monitored is the intended target area of the mammal 42, or may determine whether the ultrasonic monitoring device 10 needs to be relocated to monitor the intended target area of the mammal 42, based on relative locations of the internal structure 41 to one or more surfaces, structures, or areas within the mammal 42. If the microprocessor 48 determines that the internal structure 41 being monitored is not the intended target area of the mammal 42, or determines that the ultrasonic monitoring device 10 is not properly located, steps 202 through 208 may be repeated until it is determined that the internal structure 41 being monitored is the intended target area of the mammal 42 and the ultrasonic monitoring device 10 is properly located. During step 208, a location of the ultrasonic monitoring device 10 relative to the carotid artery 74 and the jugular vein 72 may be determined, and a determination may be made as to whether the ultrasonic monitoring device 10 is located in the desired central venous pressure monitoring location relative to the mammal 42 based on the relative location determinations.

During step 208, the microprocessor 48 may determine whether the ultrasonic monitoring device 10 has detected a transition location 92 at which a jugular vein 72 changes from a collapsed state to an expanded state, and if so, may determine a distance a+b+c+d of the transition location 92 away from a portion of a heart 179, comprising a most superior portion of the right atrium 180 of the mammal 42, and may determine a central venous pressure CVP of the mammal 42 based on the distance a+b+c+d. During step 208, the microprocessor 48 may use inclination data received by an inclinometer 47 that indicates an inclination state of the mammal 42 from the supine position. During step 208, a location and quantity of blood or fluid positioned in the jugular vein 72 may be determined, and a central venous pressure CVP of the mammal 42 may be determined based on the location and quantity of the blood or fluid. During step 208, the microprocessor 48 may execute an algorithm to determine central venous pressure CVP=sin θ*(a+b+c+d), or may execute an algorithm to determine jugular venous pressure JVP=sin θ*(b+c+d). The variables of the algorithms may be determined as previously discussed herein.

During step 210, the microprocessor 48 saves the determined physiological parameters 62, and then displays the determined physiological parameters 62 on a display 21 located on the ultrasonic monitoring device 10, or transmits them to a remote device 66 which displays them. The display 21 or remote device 66 may store the historical physiological parameters 62 to be recalled and displayed at anytime. The remote device 66 may communicate the determined physiological parameters 62 to other systems. Steps 204 through 210 may be continuously repeated for a period ranging between one to five days in order to continuously monitor the physiological parameter 62 of the mammal 42. In other embodiments, the continuously monitored time range may vary.

During step 212, if the ultrasonic monitoring device 10 determines that the physiological parameter 62 is outside of a normal range, an alert may be signaled to allow precautionary, preventative, or surgical responsive measures. During step 214, one or more portions of the ultrasonic monitoring device 10 are disposed of (i.e. thrown away) after the monitored time range, and the disposed portion of the ultrasonic monitoring device 10 is not reused. The disposed portion of the ultrasonic monitoring device 10 may comprise the entire ultrasonic monitoring device 10, or any portion thereof such as the adhesive, conformable, gel layer 22. The disposed portion of the ultrasonic monitoring device 10 may be biodegradable or remanufacturable. The ultrasonic monitoring device 10 may send an alert when the power source 46 is near its low capacity.

The ultrasonic monitoring device 10 and the method 200 of the disclosure may reduce one or more problems associated with one or more current diagnostic ultrasound devices. For instance, the ultrasonic monitoring device 10 and the method 200 ultrasonically, continuously, and non-invasively monitor the target area of the mammal in real-time at reduced expense, without requiring the monitoring to be done during a patient's stay at a medical office or hospital, in order to determine one or more physiological parameters of the target area. This is done without generating an image of the target area and without using a mechanical or electrical scanning technique. Moreover, the ultrasonic monitoring device 10 and the method 200 are able to determine whether the ultrasonic monitoring device 10 is positioned in the correct location and monitoring the intended target area. Further, one or more portions of the ultrasonic monitoring device 10 may be disposable, reducing cost associated with ultrasonically monitoring a target area. Additionally, the ultrasonic monitoring device 10 may transmit the results of the ultrasonic monitoring to a remote device to alert appropriate health-care personnel if a physiological parameter is out of range without requiring the patient to remain at a medical office or hospital. Due to the reduced cost, ease of use, and accuracy of the ultrasonic monitoring device 10, medical problems may be discovered sooner, allowing appropriate, timely medical care to be administered thereby reducing the probability of a serious health problem, resulting in reduced overall medical care, and corresponding reduced cost.

It should be understood, of course, that the foregoing relates to exemplary embodiments of the disclosure and that modifications may be made without departing from the scope of the disclosure as set forth in the following claims.

We claim:

1. A central venous pressure ultrasonic monitoring device comprising:
   a substrate;
   a plurality of ultrasonic transducer elements coupled to the substrate, wherein each ultrasonic transducer element is separately configured to transmit a signal to a jugular vein of a mammal and to receive an echo return signal from the jugular vein;
   a computer readable memory medium comprising program instructions;
   a microprocessor coupled to the plurality of ultrasonic transducer elements and to the computer readable memory medium, the microprocessor configured to execute the program instructions to determine central venous pressure of the mammal based on a combined analysis of the echo return signals received by the plurality of ultrasonic transducer elements without ultrasonically scanning the mammal or generating an ultrasonic image of the jugular vein; and
   a power source, coupled to at least one of the plurality of ultrasonic transducer elements, the computer readable memory medium, or the microprocessor, configured to supply electrical energy.

2. The central venous pressure ultrasonic monitoring device of claim 1 wherein the microprocessor configured to execute the program instructions is configured to determine, based on the combined analysis of the echo return signals received by the plurality of ultrasonic transducer elements, whether there is a transition location at which the jugular vein changes from a collapsed state to an expanded state, and if so, to determine a distance of the transition location away from a portion of a heart of the mammal, and to determine the central venous pressure of the mammal based on the distance.

3. The central venous pressure ultrasonic monitoring device of claim 1 further comprising an inclinometer coupled to the microprocessor, the microprocessor configured to execute the program instructions to determine the central venous pressure of the mammal based on the combined analysis of the echo return signals received by the plurality of ultrasonic transducer elements in conjunction with inclination data received by the inclinometer indicating an inclination state of the mammal from a supine position.

4. The central venous pressure ultrasonic monitoring device of claim 1 wherein the microprocessor configured to execute the program instructions is configured to determine, based on the combined analysis of the echo return signals received by the plurality of ultrasonic transducer elements, a location and quantity of blood positioned in the jugular vein, and to determine the central venous pressure of the mammal based on the location and the quantity of the blood.

5. The central venous pressure ultrasonic monitoring device of claim 1 wherein each ultrasonic transducer element is separately configured to transmit the signal to a carotid artery of the mammal and to receive the echo return signal from the carotid artery, and the microprocessor configured to execute the program instructions is configured to determine, based on the combined analysis of the echo return signals received by the plurality of ultrasonic transducer elements from the carotid artery and the jugular vein, a location of the central venous pressure ultrasonic monitoring device relative to the carotid artery and to the jugular vein, and whether the location is a desired central venous pressure monitoring location relative to the mammal.

6. The central venous pressure ultrasonic monitoring device of claim 1 wherein the plurality of ultrasonic transducer elements coupled to the substrate is positioned in an array comprising five to ten rows of the transducer elements and three to five columns of the transducer elements for a total of fifteen to fifty of the transducer elements.

7. The central venous pressure ultrasonic monitoring device of claim 1 wherein each ultrasonic transducer element is separately configured to transmit the signal having a voltage of approximately 75 Volts, and a frequency of approximately 10 MHz, and each ultrasonic transducer element is configured to receive the echo return signal from the jugular vein for a time ranging between 1 to 50 microseconds.

8. The central venous pressure ultrasonic monitoring device of claim 1 wherein the program instructions comprise an algorithm configured to determine the central venous pressure of the mammal based on the combined analysis of the echo return signals received by the plurality of the ultrasonic transducer elements, wherein the algorithm comprises central venous pressure $=(a+b+c+d)*(\sin\theta)$, wherein "a" = a first linear distance from a most superior portion of a right atrium of the mammal to a sternal notch of the mammal, "b" = a second linear distance from the sternal notch of the mammal to a base of a neck of the mammal, "c" = a third linear distance from the base of the neck of the mammal to a surface of the central venous pressure ultrasonic monitoring device which is closest to the base of the neck of the mammal when the central venous pressure ultrasonic monitoring device is attached to a skin of the mammal and transmitting the signal, "d" = a fourth linear distance from the surface of the central venous pressure ultrasonic monitoring device which is closest to the base of the mammal, when the central venous pressure ultrasonic monitoring device is attached to the skin of the mammal and transmitting the signal, to a transition location at which the jugular vein of the mammal changes from a collapsed state to an expanded state, and "$\theta$" = an inclination angle of the mammal from a supine position.

9. A method of monitoring central venous pressure of a mammal comprising:
   positioning a central venous pressure ultrasonic monitoring device against skin of a mammal;
   transmitting separate signals from a plurality of ultrasonic transducer elements of the central venous pressure ultrasonic monitoring device to a jugular vein of the mammal;
   receiving, with the plurality of ultrasonic transducer elements, echo return signals from the jugular vein of the mammal; and
   determining the central venous pressure of the mammal using a microprocessor to execute program instructions to process a combined analysis of the echo return signals received by the plurality of transducer elements without ultrasonically scanning the mammal or generating an ultrasonic image of the jugular vein.

10. The method of claim 9 wherein the determining step further comprises determining, based on the combined analysis of the echo return signals received by the plurality of ultrasonic transducer elements, whether there is a transition location at which the jugular vein changes from a collapsed state to an expanded state, and if so, determining a distance of the transition location away from a portion of a heart of the mammal, and determining the central venous pressure of the mammal based on the distance.

11. The method of claim 9 wherein the determining step further comprises determining the central venous pressure of the mammal based on the combined analysis of the echo return signals received by the plurality of ultrasonic transducer elements in conjunction with inclination data received by an inclinometer indicating an inclination state of the mammal from a supine position.

12. The method of claim 9 wherein the determining step further comprises determining, based on the combined analysis of the echo return signals received by the plurality of ultrasonic transducer elements, a location and quantity of blood positioned in the jugular vein, and determining the central venous pressure of the mammal based on the location and the quantity of the blood.

13. The method of claim 9 wherein the transmitting step further comprises transmitting the separate signals to a carotid artery of the mammal, the receiving step further comprises receiving the echo return signals from the carotid artery of the mammal, and the determining step further comprises determining, based on the combined analysis of the echo return signals received by the plurality of ultrasonic transducer elements from the carotid artery and the jugular vein, a location of the central venous pressure ultrasonic monitoring device relative to the carotid artery and to the jugular vein, and determining whether the location is a desired central venous pressure monitoring location relative to the mammal.

14. The method of claim 9 wherein the transmitting step further comprises transmitting the separate signals from the plurality of ultrasonic transducer elements of the central venous pressure ultrasonic monitoring device at a voltage of approximately 75 Volts, and a frequency of approximately 10 MHz, and the receiving step further comprises receiving, with the plurality of ultrasonic transducer elements, the echo return signals from the jugular vein of the mammal for a time ranging between 1 to 50 microseconds.

15. The method of claim 9 further comprising transmitting the determined central venous pressure to a display device, and displaying the determined central venous pressure with the display device.

16. The method of claim 9 wherein the determining the central venous pressure of the mammal using the microprocessor to execute the program instructions to process the combined analysis of the echo return signals received by the plurality of transducer elements comprises an algorithm determining the central venous pressure of the mammal, wherein the algorithm comprises central venous pressure $=(a+b+c+d)*(\sin\theta)$, wherein "a" =a first linear distance from a most superior portion of a right atrium of the mammal to a sternal notch of the mammal, "b" =a second linear distance from the sternal notch of the mammal to a base of a neck of the mammal, "c" =a third linear distance from the base of the neck of the mammal to a surface of the central venous pressure ultrasonic monitoring device which is closest to the base of the neck of the mammal as the central venous pressure ultrasonic monitoring device is positioned against the skin of the mammal and transmitting the separate signals, "d" =a fourth linear distance from the surface of the central venous pressure ultrasonic monitoring device which is closest to the base of the neck of the mammal, when the central venous pressure ultrasonic monitoring device is placed against the skin of the mammal and transmitting the separate signals, to a transition location at which the jugular vein of the mammal changes from a collapsed state to an expanded state, and "θ" =an inclination angle of the mammal from a supine position.

17. The method of claim 9 further comprising continuously monitoring the central venous pressure of the mammal for a period of one to five days.

18. A jugular venous pressure ultrasonic monitoring device comprising:
a substrate;
a plurality of ultrasonic transducer elements coupled to the substrate, wherein each ultrasonic transducer element is separately configured to transmit a signal to a jugular vein of a mammal and to receive an echo return signal from the jugular vein;
a computer readable memory medium comprising program instructions;
a microprocessor coupled to the plurality of ultrasonic transducer elements and to the computer readable memory medium, the microprocessor configured to execute the program instructions to determine jugular venous pressure of the mammal based on a combined analysis of the echo return signals received by the plurality of ultrasonic transducer elements without ultrasonically scanning the mammal or generating an ultrasonic image of the jugular vein; and
a power source, coupled to at least one of the plurality of ultrasonic transducer elements, the computer readable memory medium, or the microprocessor, configured to supply electrical energy.

19. The jugular venous pressure ultrasonic monitoring device of claim 18 wherein the program instructions comprise an algorithm configured to determine the jugular venous pressure of the mammal based on the combined analysis of the echo return signals received by the plurality of the ultrasonic transducer elements, wherein the algorithm comprises jugular venous pressure $=\sin\theta*(b+c+d)$, wherein "b" =a first linear distance from a sternal notch of the mammal to a base of a neck of the mammal, "c" =a second linear distance from the base of the neck of the mammal to a surface of the jugular venous pressure ultrasonic monitoring device which is closest to the base of the neck of the mammal when the jugular venous pressure ultrasonic monitoring device is attached to a skin of the mammal and transmitting the signal, "d" =a third linear distance from the surface of the jugular venous pressure ultrasonic monitoring device which is closest to the base of the mammal, when the jugular venous pressure ultrasonic monitoring device is attached to the skin of the mammal and transmitting the signal, to a transition location at which the jugular vein of the mammal changes from a collapsed state to an expanded state, and "θ" =an inclination angle of the mammal from a supine position.

20. A central venous pressure ultrasonic monitoring device comprising:
a substrate;
a plurality of ultrasonic transducer elements coupled to the substrate, wherein each ultrasonic transducer element is separately configured to transmit a signal to a jugular vein of a mammal and to receive an echo return signal from the jugular vein;
a computer readable memory medium comprising program instructions;
a microprocessor coupled to the plurality of ultrasonic transducer elements and to the computer readable memory medium, the microprocessor configured to execute the program instructions to determine central venous pressure of the mammal based on a combined analysis of the echo return signals received by the plurality of ultrasonic transducer elements; and
a power source, coupled to at least one of the plurality of ultrasonic transducer elements, the computer readable memory medium, or the microprocessor, configured to supply electrical energy;
wherein each ultrasonic transducer element is separately configured to transmit the signal to a carotid artery of the mammal and to receive the echo return signal from the carotid artery, and the microprocessor configured to execute the program instructions is configured to determine, based on the combined analysis of the echo return signals received by the plurality of ultrasonic transducer elements from the carotid artery and the jugular vein, a location of the central venous pressure ultrasonic monitoring device relative to the carotid artery and to the jugular vein, and whether the location is a desired central venous pressure monitoring location relative to the mammal.

21. A central venous pressure ultrasonic monitoring device comprising:
a substrate;
a plurality of ultrasonic transducer elements coupled to the substrate, wherein each ultrasonic transducer element is separately configured to transmit a signal to a jugular vein of a mammal and to receive an echo return signal from the jugular vein;
a computer readable memory medium comprising program instructions;
a microprocessor coupled to the plurality of ultrasonic transducer elements and to the computer readable memory medium, the microprocessor configured to execute the program instructions to determine central venous pressure of the mammal based on a combined analysis of the echo return signals received by the plurality of ultrasonic transducer elements; and
a power source, coupled to at least one of the plurality of ultrasonic transducer elements, the computer readable memory medium, or the microprocessor, configured to supply electrical energy;

wherein the program instructions comprise an algorithm configured to determine the central venous pressure of the mammal based on the combined analysis of the echo return signals received by the plurality of the ultrasonic transducer elements, wherein the algorithm comprises central venous pressure $=(a+b+c+d)*(\sin\theta)$, wherein "a" = a first linear distance from a most superior portion of a right atrium of the mammal to a sternal notch of the mammal, "b" = a second linear distance from the sternal notch of the mammal to a base of a neck of the mammal, "c" = a third linear distance from the base of the neck of the mammal to a surface of the central venous pressure ultrasonic monitoring device which is closest to the base of the neck of the mammal when the central venous pressure ultrasonic monitoring device is attached to a skin of the mammal and transmitting the signal, "d" = a fourth linear distance from the surface of the central venous pressure ultrasonic monitoring device which is closest to the base of the mammal, when the central venous pressure ultrasonic monitoring device is attached to the skin of the mammal and transmitting the signal, to a transition location at which the jugular vein of the mammal changes from a collapsed state to an expanded state, and "$\theta$" = an inclination angle of the mammal from a supine position.

\* \* \* \* \*